United States Patent
Li

(10) Patent No.: US 12,324,856 B2
(45) Date of Patent: Jun. 10, 2025

(54) ORAL DRUG DOSAGE FORM COMPRISING DRUG IN THE FORM OF NANOPARTICLES

(71) Applicant: Triastek, Inc., Nanjing (CN)

(72) Inventor: Xiaoling Li, Dublin, CA (US)

(73) Assignee: Triastek, Inc., Nanjing (CN)

( * ) Notice: Subject to any disclaimer, the term of this patent is extended or adjusted under 35 U.S.C. 154(b) by 134 days.

(21) Appl. No.: 17/197,204

(22) Filed: Mar. 10, 2021

(65) Prior Publication Data
US 2021/0205226 A1   Jul. 8, 2021

Related U.S. Application Data

(60) Division of application No. 16/289,499, filed on Feb. 28, 2019, now Pat. No. 10,973,767, which is a continuation of application No. 16/028,305, filed on Jul. 5, 2018, now Pat. No. 10,258,575, which is a continuation of application No. 15/173,596, filed on Jun. 3, 2016, now Pat. No. 10,363,220.

(60) Provisional application No. 62/313,092, filed on Mar. 24, 2016, provisional application No. 62/296,087, filed on Feb. 17, 2016, provisional application No. 62/170,645, filed on Jun. 3, 2015.

(51) Int. Cl.
*A61K 9/20* (2006.01)
*A61K 9/00* (2006.01)
*A61K 9/24* (2006.01)
*A61K 31/192* (2006.01)

(52) U.S. Cl.
CPC .......... *A61K 9/2031* (2013.01); *A61K 9/0065* (2013.01); *A61K 9/2027* (2013.01); *A61K 9/2072* (2013.01); *A61K 9/209* (2013.01); *A61K 31/192* (2013.01)

(58) Field of Classification Search
CPC .... A61K 9/2072; A61K 9/2086; A61K 9/209; A61K 9/2095
See application file for complete search history.

(56) References Cited

U.S. PATENT DOCUMENTS

| | | | |
|---|---|---|---|
| 3,823,816 A | 7/1974 | Controulis et al. | |
| 4,735,804 A | 4/1988 | Caldwell et al. | |

(Continued)

FOREIGN PATENT DOCUMENTS

| | | | | |
|---|---|---|---|---|
| AU | 782141 B2 * | 7/2005 | ........... | A61K 9/0056 |
| CN | 103948557 A | 7/2004 | | |

(Continued)

OTHER PUBLICATIONS

Anonymous (Aug. 1997). "Guidance for Industry: Dissolution Testing of Immediate Release Solid Oral Dosage Forms," Center for Drug Evaluation and Research, U.S. Food & Drug Administration. FDA-1997-D-0187, 17 pages.

(Continued)

*Primary Examiner* — Michael B. Pallay
(74) *Attorney, Agent, or Firm* — MORRISON & FOERSTER LLP

(57) ABSTRACT

The present disclosure provides a stable solid pharmaceutical dosage form for oral administration. The dosage form includes a substrate that forms at least one compartment and a drug content loaded into the compartment. The dosage form is so designed that the active pharmaceutical ingredient of the drug content is released in a controlled manner.

19 Claims, 20 Drawing Sheets

(56) References Cited

U.S. PATENT DOCUMENTS

| | | |
|---|---|---|
| 5,198,229 A | 3/1993 | Wong |
| 5,204,055 A | 4/1993 | Sachs |
| 5,260,009 A | 11/1993 | Penn |
| 5,340,656 A | 8/1994 | Sachs |
| 5,342,624 A | 8/1994 | Mcneill |
| 5,387,380 A | 2/1995 | Cima |
| 5,490,962 A | 2/1996 | Cima |
| 5,503,785 A | 4/1996 | Crump |
| 5,518,690 A | 5/1996 | Masahashi |
| 5,543,155 A | 8/1996 | Fekete |
| 5,633,021 A | 5/1997 | Brown |
| 5,869,170 A | 2/1999 | Cima |
| 6,264,985 B1 | 7/2001 | Cremer |
| 6,280,771 B1 | 8/2001 | Monkhouse |
| 6,294,200 B1 | 9/2001 | Conte et al. |
| 6,471,992 B1 | 10/2002 | Yoo |
| 6,514,518 B2 | 2/2003 | Monkhouse |
| 6,530,958 B1 | 3/2003 | Cima |
| 6,582,726 B1 | 6/2003 | Geysen |
| 6,685,962 B2 | 2/2004 | Friedman |
| 6,890,547 B1 | 5/2005 | Takada et al. |
| 7,163,693 B1 | 1/2007 | Clarke |
| 7,276,252 B2 | 10/2007 | Payumno |
| 7,300,668 B2 | 11/2007 | Pryce Lewis |
| 7,314,640 B2 | 1/2008 | Sriwongjanya |
| 7,820,201 B2 | 10/2010 | Pryce Lewis |
| 7,875,290 B2 | 1/2011 | Payumo |
| 7,931,914 B2 | 4/2011 | Pryce Lewis |
| 8,088,415 B2 | 1/2012 | Wang |
| 8,465,777 B2 | 6/2013 | Wang |
| 8,673,352 B2 | 3/2014 | Sowden |
| 8,758,658 B2 | 6/2014 | Pryce Lewis |
| 8,828,411 B2 | 9/2014 | Yoo |
| 9,114,072 B2 | 8/2015 | Yoo |
| 9,314,429 B2 | 4/2016 | Jacob |
| 9,339,489 B2 | 5/2016 | Jacob |
| 10,143,626 B2 | 12/2018 | Li |
| 10,201,503 B1 | 2/2019 | Li |
| 10,258,575 B2 | 4/2019 | Li |
| 10,350,822 B1 | 7/2019 | Deng |
| 10,363,220 B2 | 7/2019 | Li |
| 10,624,857 B2 | 4/2020 | Li |
| 10,973,767 B2 | 4/2021 | Li |
| 11,278,499 B2 | 3/2022 | Li |
| 11,292,193 B2 | 4/2022 | Liu et al. |
| 11,364,674 B2 | 6/2022 | Cheng et al. |
| 11,383,439 B1 | 7/2022 | Liu |
| 11,458,684 B2 | 10/2022 | Liu et al. |
| 11,571,391 B2 | 2/2023 | Deng et al. |
| 11,612,569 B2 | 3/2023 | Li et al. |
| 12,042,562 B2 | 7/2024 | Li |
| 12,102,721 B2 | 10/2024 | Cheng et al. |
| 12,103,231 B2 | 10/2024 | Deng |
| 12,156,945 B2 | 12/2024 | Li |
| 12,168,538 B2 | 12/2024 | Wang et al. |
| 2001/0051185 A1 | 12/2001 | Faour |
| 2002/0015728 A1 | 2/2002 | Payumno |
| 2002/0106412 A1 | 8/2002 | Rowe |
| 2003/0143268 A1 | 7/2003 | Pryce Lewis |
| 2003/0147952 A1 | 8/2003 | Lim |
| 2003/0198677 A1 | 10/2003 | Pryce Lewis |
| 2004/0005360 A1 | 1/2004 | Wang |
| 2005/0249798 A1 | 11/2005 | Mohammad |
| 2006/0099257 A1 | 5/2006 | Langridge et al. |
| 2006/0210630 A1 | 9/2006 | Liang et al. |
| 2006/0233881 A1 | 10/2006 | Sowden |
| 2008/0220061 A1 | 9/2008 | Pryce Lewis |
| 2008/0311191 A1 | 12/2008 | Nangia et al. |
| 2009/0148514 A1 | 6/2009 | Matthews |
| 2009/0317465 A1* | 12/2009 | Peppas ............ A61K 9/2095 424/472 |
| 2010/0003332 A1* | 1/2010 | Bae ............ A61K 9/5192 514/569 |
| 2010/0226855 A1 | 9/2010 | Nangia |
| 2010/0233253 A1* | 9/2010 | Kavimandan ........ A61K 31/41 424/464 |
| 2011/0111022 A1 | 5/2011 | Kim et al. |
| 2011/0187015 A1 | 8/2011 | Pryce Lewis |
| 2011/0262496 A1 | 10/2011 | Desai |
| 2012/0315333 A1 | 12/2012 | Zhou |
| 2013/0039960 A1 | 2/2013 | Desai |
| 2013/0149379 A1 | 6/2013 | Berner |
| 2013/0193621 A1 | 8/2013 | Daya et al. |
| 2013/0337148 A1 | 12/2013 | Yang |
| 2013/0344149 A1 | 12/2013 | Stefan |
| 2014/0271842 A1 | 9/2014 | Herbig et al. |
| 2015/0366801 A1 | 12/2015 | Jacob |
| 2016/0354315 A1 | 12/2016 | Li |
| 2017/0027872 A1 | 2/2017 | Wen |
| 2018/0116911 A1 | 5/2018 | Li |
| 2018/0214383 A1 | 8/2018 | Sun et al. |
| 2018/0311167 A1 | 11/2018 | Li |
| 2019/0192440 A1 | 6/2019 | Li |
| 2019/0209468 A1 | 7/2019 | Deng |
| 2019/0209482 A1 | 7/2019 | Li |
| 2019/0321299 A1 | 10/2019 | Li |
| 2020/0315971 A1 | 10/2020 | Li |
| 2020/0338009 A1 | 10/2020 | Li |
| 2021/0077410 A1 | 3/2021 | Deng et al. |
| 2021/0078244 A1 | 3/2021 | Deng et al. |
| 2021/0128479 A1 | 5/2021 | Cheng et al. |
| 2021/0154910 A1 | 5/2021 | Cheng et al. |
| 2021/0178677 A1 | 6/2021 | Liu et al. |
| 2021/0196638 A1 | 7/2021 | Deng et al. |
| 2022/0118698 A1 | 4/2022 | Deng et al. |
| 2022/0212404 A1 | 7/2022 | Liu et al. |
| 2022/0212408 A1 | 7/2022 | Liu et al. |
| 2022/0339857 A1 | 10/2022 | Cheng et al. |
| 2023/0048362 A1 | 2/2023 | Liu et al. |
| 2023/0070928 A1 | 3/2023 | Wang et al. |
| 2023/0225978 A1 | 7/2023 | Li et al. |
| 2023/0390193 A1 | 12/2023 | Deng |
| 2023/0398066 A1 | 12/2023 | Deng et al. |
| 2024/0041779 A1 | 2/2024 | Deng |
| 2024/0180840 A1 | 6/2024 | Cao |
| 2024/0316864 A1 | 9/2024 | Deng |
| 2024/0342094 A1 | 10/2024 | Li |
| 2024/0408023 A1 | 12/2024 | Cheng |

FOREIGN PATENT DOCUMENTS

| | | |
|---|---|---|
| CN | 1216597 C | 8/2005 |
| CN | 101370483 A | 2/2009 |
| CN | 1620284 B | 4/2010 |
| CN | 105687153 A | 6/2016 |
| CN | 205343831 U | 6/2016 |
| CN | 106491551 A | 3/2017 |
| CN | 106535878 A | 3/2017 |
| CN | 107019676 A | 8/2017 |
| CN | 108215153 A | 6/2018 |
| CN | 108215154 A | 6/2018 |
| CN | 207669820 U | 7/2018 |
| CN | 207901677 U | 9/2018 |
| CN | 105690762 A | 6/2019 |
| CN | 110787145 A | 2/2020 |
| CN | 111249257 A | 6/2020 |
| CN | 109432039 B | 5/2021 |
| EP | 0631775 A1 | 1/1995 |
| EP | 1112739 A1 | 7/2001 |
| EP | 3302442 A1 | 4/2018 |
| EP | 3626439 A1 | 3/2020 |
| GB | 436236 A | 10/1935 |
| JP | H09221416 A | 8/1997 |
| JP | 2010523554 A | 7/2010 |
| JP | 2020506918 A | 3/2020 |
| JP | 2020507556 A | 3/2020 |
| KR | 102078805 B1 | 2/2020 |
| WO | 199009168 A1 | 8/1990 |
| WO | 199213521 A1 | 8/1992 |
| WO | 199836738 A1 | 8/1998 |
| WO | 199836739 A1 | 8/1998 |
| WO | 2000015199 A1 | 3/2000 |
| WO | 200038650 A1 | 7/2000 |

(56) References Cited

FOREIGN PATENT DOCUMENTS

| | | |
|---|---|---|
| WO | 200105406 A1 | 1/2001 |
| WO | 200137812 A2 | 5/2001 |
| WO | 200137813 A2 | 5/2001 |
| WO | 200187272 A2 | 11/2001 |
| WO | 200197783 A1 | 12/2001 |
| WO | 2003037244 A2 | 5/2003 |
| WO | 2003037607 A1 | 5/2003 |
| WO | 2003041690 A2 | 5/2003 |
| WO | 2003092633 A2 | 11/2003 |
| WO | 2004112755 A1 | 12/2004 |
| WO | 2005027878 A1 | 3/2005 |
| WO | 2006058247 A2 | 6/2006 |
| WO | 2007078290 A1 | 7/2007 |
| WO | 2008122966 A2 | 10/2008 |
| WO | 2009050189 A2 | 4/2009 |
| WO | 2009084040 A1 | 7/2009 |
| WO | 2009101658 A1 | 8/2009 |
| WO | 2009144558 A1 | 12/2009 |
| WO | 2014143935 A1 | 9/2014 |
| WO | 2014144512 A1 | 9/2014 |
| WO | 2014144661 A1 | 9/2014 |
| WO | 2014197999 A1 | 12/2014 |
| WO | 2015077262 A1 | 5/2015 |
| WO | 2015095230 A1 | 6/2015 |
| WO | 2015136377 A2 | 9/2015 |
| WO | 2015187746 A1 | 12/2015 |
| WO | 2016025762 A1 | 2/2016 |
| WO | 2016075497 A1 | 5/2016 |
| WO | 2016192680 A1 | 12/2016 |
| WO | 2017152974 A1 | 9/2017 |
| WO | 2017153846 A2 | 9/2017 |
| WO | 2017193099 A1 | 11/2017 |
| WO | 2018137686 A1 | 8/2018 |
| WO | 2018210183 A1 | 11/2018 |
| WO | 2019025869 A1 | 2/2019 |
| WO | 2019137199 A1 | 7/2019 |
| WO | 2019137200 A1 | 7/2019 |
| WO | 2019137333 A1 | 7/2019 |
| WO | 2019224058 A1 | 11/2019 |
| WO | 2021031824 A1 | 2/2021 |
| WO | 2021042865 A1 | 3/2021 |
| WO | 2021164660 A1 | 8/2021 |
| WO | 2022007570 A1 | 1/2022 |
| WO | 2022089631 A1 | 5/2022 |
| WO | 2022121927 A1 | 6/2022 |
| WO | 2022193922 A2 | 9/2022 |
| WO | 2024083145 A1 | 4/2024 |
| WO | 2024199448 A1 | 10/2024 |

OTHER PUBLICATIONS

Brooke, D. et al. (Feb. 1977). "Zero-Order Drug Delivery System: Theory and Preliminary Testing," J. Pharm Sci. 66(2):159-162.
International Search Report, mailed Aug. 29, 2016 for PCT Application No. PCT/CN2016/084838, filed Jun. 3, 2016, 4 pages.
Gibson, I. et al. (2015). "Additive Manufacturing Technologies: 3D Printing, Rapid Prototyping, and Direct Digital Manufacturing," 2nd ed. Johnson Matthey Technol. Rev. 59(3):193-198.
Goole, J. et al. (Feb. 2016, e-pub. Jan. 3, 2016). "3D printing in Pharmaceutics: A New Tool for Designing Customized Drug Delivery Systems," Int. J. Pharm. 499(1-2):376-394.
Goyanes, A. et al. (2015). "3D Printing: Engineering Novel Oral Devices With Unique Design and Drug Release Characteristics," Molecular Pharmaceutics 12(11):3783-4174, 24 pages.
International Preliminary Report on Patentability issued Jul. 30, 2019, for PCT Application No. PCT/CN2018/074146, filed Jan. 25, 2018, 5 pages.
International Preliminary Report on Patentability, issued Dec. 5, 2017 for PCT Application No. PCT/CN2016/084838, filed Jun. 3, 2016, 5 pages.
International Search Report and Written Opinion, mailed Apr. 26, 2018, for PCT Application No. PCT/CN2018/074146, filed Jan. 25, 2018, 9 pages.
Katstra, W.E. et al. (Jun. 2001). Fabrication of Complex Oral Delivery Forms by Three Dimensional Printing™, Dissertation in Materials Science and Engineering, Massachusetts Institute of Technology.
Katstra, W.E. et al. (May 3, 2000). "Oral Dosage Forms Fabricated by Three Dimensional Printing," J. Control Release 66:1-9.
Khaled, S.A. et al. (2015). "3D Printing of Five-in-One Dose Combination Polypill With Defined Immediate and Sustained Release Profiles," School of Pharmacy, The University of Nottingham 217:308-314, 21 pages.
Khaled, S.A. et al. (Oct. 30, 2015, e-pub. Jul. 30, 2015). "3D Printing of Tablets Containing Multiple Drugs With Defined Release Profiles," Int. J. Pharm 494(2):643-650.
Lipper, R.A. et al. (Feb. 1977). "Analysis of Theoretical Behavior of a Proposed Zero-Order Drug Delivery System," J. Pharm Sci. 66(2):163-164.
Melchels, F.P.W. et al. (2010). "A Review on Stereolithography and Its Application in Biomedical Engineering," Biomaterials 31:6121-6130, 22 pages.
Rowe C.W. et al. (May 3, 2000). "Multimechanism oral Dosage Forms Fabricated by Three Dimensional PrintingTM" Journal of Controlled Release 66(1):11-17.
Srikonda, S. et al. (2006). "Osmotic Controlled Drug Delivery Systems," Chapter 7 in Design of Controlled Release Drug Delivery Systems, pp. 203-230.
U.S. Appl. No. 16/481,036, filed Jul. 25, 2019, for Cheng et al. (Copy not submitted herewith pursuant to the waiver of 37 C.F.R. § 1.98(a)(2)(iii) issued by the Office on Sep. 21, 2004).
U.S. Appl. No. 16/614,301, filed Nov. 15, 2019, for Cheng et al. (Copy not submitted herewith pursuant to the waiver of 37 C.F.R. § 1.98(a)(2)(iii) issued by the Office on Sep. 21, 2004).
Written Opinion of the International Searching Authority, mailed Aug. 29, 2016 for PCT Application No. PCT/CN2016/084838, filed Jun. 3, 2016, 4 pages.
Abdul, S. et al. (2004). "A Flexible Technology for Modified Release of Drugs: Multi-Layered Tablets," Journal of Controlled Release 97:393-405.
Hatton, G.B. et al. (2015, e-pub Feb. 24, 2015). "Animal Farm: Considerations in Animal Gastrointestinal Physiology and Relevance to Drug Delivery in Humans," J Pharm Sci., 30 pages.
International Search Report and Written Opinion, mailed Jan. 30, 2022, for PCT Application No. PCT/CN2021/127852, filed Nov. 1, 2021, 15 pages.
International Search Report and Written Opinion, mailed Mar. 9, 2022, for PCT Application No. PCT/CN2021/136353, filed Dec. 8, 2021, 14 pages.
Meyer, D.M. et al. (2010). "Anti-Inflammatory Activity and Neutrophil Reductions Mediated by the JAK1/JAK3 Inhibitor, CP-690,550, in Rat Adjuvant-Induced Arthritis," J. Inflammation 7:41, 12 pages.
Rawlings, J.S. et al. (2004). "The JAK/STAT Signaling Pathway," J. Cell Sci. 117(8):1281-1283.
Schwartz, L. et al. (Jan. 1, 2017). "The Warburg Effect and the Hallmarks of Cancer," Nat Rev Drug Discov. 17(2):164-170, 26 pages.
Shende, P. et al. (2012). "Multi-Layer Tablet: Current Scenario and Recent Advances," International Journal of Drug Delivery 4:418-426.
Thakral, S. et al. (2013). "Eudragit®: A Technology Evaluation," Expert Opin. Drug Deliv. 10(1):131-149.
Yoshida, T. et al. (Nov. 2013). "pH- and Ion-Sensitive Polymers For Drug Delivery," Expert Opinion Drug Delivery 10(11):1497-1513, 28 pages.
Alhnan, M.A. et al. (Aug. 2016, e-published on May 18, 2016). "Emergence of 3D Printed Dosage Forms: Opportunities and Challenges," Pharm. Res. 33(8):1817-1832, 16 pages.
Cole, G. (1995). Pharmaceutical Coating Technology, Taylor & Francis Publishers, 574 pages.
Ross, A.C. et al. (Feb. 18, 2000). "Chronopharmaceutical Drug Delivery from a Pulsatile Capsule Device Based on Programmable Erosion," Journal of Pharmacy and Pharmacology 52(8):903-909.
U.S. Appl. No. 18/034,004, filed Apr. 26, 2023, for Deng et al. (Copy not submitted herewith pursuant to the waiver of 37 C.F.R. § 1.98(a)(2)(iii) issued by the Office on Sep. 21, 2004).

(56) References Cited

OTHER PUBLICATIONS

U.S. Appl. No. 18/256,035, filed Jun. 5, 2023, for Deng et al. (Copy not submitted herewith pursuant to the waiver of 37 C.F.R. § 1.98(a)(2)(iii) issued by the Office on Sep. 21, 2004).

U.S. Appl. No. 18/550,432, filed Sep. 13, 2023, for Cao et al. (Copy not submitted herewith pursuant to the waiver of 37 C.F.R. § 1.98(a)(2)(iii) issued by the Office on Sep. 21, 2004).

Kempin, W. et al. (2018, e-pub. Apr. 20, 2018). "Immediate Release 3D-Printed Tablets Produced Via Fused Deposition Modeling of a Thermo-Sensitive Drug," Pharm. Res. 35:124, 12 pages.

U.S. Appl. No. 18/732,210, filed Jun. 3, 2024, for Cao et al. (Copy not submitted herewith pursuant to the waiver of 37 C.F.R. § 1.98(a)(2)(iii) issued by the Office on Sep. 21, 2004).

U.S. Appl. No. 18/740,160, filed Jun. 11, 2024, for Xiaoling Li. (Copy not submitted herewith pursuant to the waiver of 37 C.F.R. § 1.98(a)(2)(iii) issued by the Office on Sep. 21, 2004).

U.S. Appl. No. 18/810,262, filed Aug. 20, 2024, for Cheng et al. (Copy not submitted herewith pursuant to the waiver of 37 C.F.R. § 1.98(a)(2)(iii) issued by the Office on Sep. 21, 2004).

U.S. Appl. No. 18/926,252, filed Oct. 24, 2024, for Wang et al. (Copy not submitted herewith pursuant to the waiver of 37 C.F.R. § 1.98(a)(2)(iii) issued by the Office on Sep. 21, 2004).

U.S. Appl. No. 18/927,582, filed Oct. 25, 2024, for Li et al. (Copy not submitted herewith pursuant to the waiver of 37 C.F.R. § 1.98(a)(2)(iii) issued by the Office on Sep. 21, 2004).

Khaled, S.A. et al. (Jan. 30, 2014). "Desktop 3D Printing of Controlled Release Pharmaceutical Bilayer Tablets," International Journal of Pharmaceutics 461(1-2):105-111, 17 pages.

Klausner, E.A. et al. (Jun. 24, 2003). "Expandable Gastroretentive Dosage Forms," Journal of Controlled Release 90(2):143-162.

Kushner, J. et al. (2020, e-pub. Dec. 19, 2019). "Development and Validation of a Level A in-vitro in-vivo Correlation for Tofacitinib Modified-Release Tablets Using Extrudable Core System Osmotic Delivery Technology," European Journal of Pharmaceutical Sciences 147:105200, 13 pages.

* cited by examiner

ORAL DRUG DOSAGE FORM COMPRISING DRUG IN THE FORM OF NANOPARTICLES

CROSS-REFERENCE TO RELATED APPLICATIONS

This application is a divisional of U.S. patent application Ser. No. 16/289,499, filed Feb. 28, 2019, now U.S. Pat. No. 10,973,767, issued Apr. 13, 2021, which is a continuation of U.S. patent application Ser. No. 16/028,305, filed Jul. 5, 2018, now U.S. Pat. No. 10,258,575, issued Apr. 16, 2019, which is a continuation of U.S. patent application Ser. No. 15/173,596, filed Jun. 3, 2016, now U.S. Pat. No. 10,363,220, issued Jul. 30, 2019, which claims priority to U.S. Provisional Patent Application Ser. Nos. 62/170,645, filed Jun. 3, 2015, 62/296,087, filed Feb. 17, 2016, and 62/313,092, filed Mar. 24, 2016, the contents of each of which are incorporated herein by reference in their entireties.

FIELD OF THE INVENTION

The present invention generally relates to a pharmaceutical dosage form and controlled release of biologically active agents, diagnostic agents, reagents, cosmetic agents, and agricultural/insecticide agents.

BACKGROUND

Pharmaceutical drug products must be manufactured into dosage forms in order to be marketed for use. Conventional dosage forms typically involve a mixture of active pharmaceutical ingredients and inactive components (excipients), along with other non-reusable materials such as a capsule shell. Categories of dosage forms include liquid dosage forms (e.g., solutions, syrups, elixirs, suspensions and emulsions), solid dosage forms (e.g., tablets, capsules, caplets and gel-caps), and semi-solid dosage form (e.g., ointments and suppositories), among which solid dosage forms are more advantages to administer drugs in systemic effect through oral route.

Tablets are most commonly used solid dosage forms, which shows more benefits in terms of manufacturing, packaging and shipping, and easy to identify and swallow. After being administered into a living organism, a tablet undergoes interplay with the body in exerting pharmaceutical effects. The active pharmaceutical ingredient must be released from the tablet before being absorbed into the blood circulation. The pharmaceutical ingredient then disperses, disintegrates or dissolves throughout the fluids and tissues of the body. During drug absorption, disposition, metabolism, and elimination process, dosage forms play a critical role in determining the release profile and bioavailability of the drugs. Therefore, there is a continuing needs for developing dosage forms that provides controlled drug delivery systems, which may offer desired drug plasma levels, reduced side effects as well as improved patient compliance.

BRIEF SUMMARY OF THE INVENTION

In one aspect, the present disclosure provides a dosage form including a substrate forming at least one compartment and a drug content loaded into the compartment. In certain embodiments, the drug content is operably linked to the substrate. In certain embodiments, the drug content is detached from the substrate and freely movable in the compartment.

In certain embodiments, the substrate is made from a thermoplastic material selected from the group consisting of a hydrophilic polymer, a hydrophobic polymer, a swellable polymer, a non-swellable polymer, a porous polymer, a non-porous polymer, an erodible polymer, a non-erodible polymer. In certain embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), Polyoxyl 40 Hydrogenerated Castor Oil, Methyl cellulose (MC), Ethyl cellulose (EC), Poloxamer, hydroxypropyl methylcellulose phthalate (HPMCP), Poloxamer, Hydrogenated Castor & Soybean Oil, Glyceryl Palmitostearate, Carnauba Wax, polylactic acid (PLA), polyglycolic acid (PGA), Cellulose acetate butyrate (CAB), Colloidal Silicon, Dioxide, Sucrose, Glucose, Polyvinyl Acetate Phthalate (PVAP) and a combination thereof.

In certain embodiments, the compartment has a shape selected from the group consisting of a pie shape, a cone shape, a pyramid shape, a cylindrical shape, a cubic or cuboidal shape, a triangular or polygonal prism shape, a tetrahedron and a combination thereof.

In certain embodiments, the first drug content is in a form of nanoparticles, microneedles or forms a net.

In certain embodiments, the drug content comprises an active pharmaceutical ingredient (API). In certain embodiments, the API is selected from the groups consisting of local anesthetics, antiepileptic drugs and anticonvulsants, anti-Alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, hormone drugs and contraceptive drugs, hypoglycemic drugs, anti-osteoporosis drugs, antibiotics, sulfonamides, quinolones, and other synthetic antibacterial drugs, anti-tuberculosis drugs, antiviral drugs, antineoplasm drugs, immune-modulators, cosmetically active agents and traditional Chinese medicine. In certain embodiments, the API is a biologically active agent, a diagnostic agent, a reagent for scientific research, a cosmetic agent, or an agricultural/insecticide agent.

In certain embodiments, the drug content further comprises an excipient. In certain embodiments, the excipient is made from materials selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructo-oligosaccharides, water-soluble oligomers and polymers and a combination thereof.

In certain embodiments, the compartment has an aperture that is blocked and/or sealed by a plug. In certain embodiments, the plug is made from a porous polymer, an erodible polymer, a pH sensitive polymer or natural occurring material such as shellac. In certain embodiments, the plug is made from a material selected from the group consisting of water-soluble polymers, erodible or dissolvable polymers, wax like materials or saccharides or any materials mentioned above.

In certain embodiments, the dosage form comprises a gas-generating component loaded into the first compartment. In certain embodiments, the gas-generating component is selected from the group consisting of water-soluble carbonates, sulphites, bicarbonates, sodium carbonate, sodium bicarbonate, sodium metabisulphite, calcium carbonate, and combinations thereof, which on contact with gastric fluid releases carbon dioxide or sulphur dioxide gas. In certain embodiments, the gas-generating component is a combination of sodium bicarbonate and organic acid (e.g., citric acid, tartaric acid etc).

In another aspect, the present disclosure provides a dosage form including a substrate forming at least a first compartment and a second compartment. The dosage form includes a first drug content loaded into the first compartment and a second drug content loaded into the second compartment.

In certain embodiments, the first compartment and the second compartment are connected. In certain embodiments, the first compartment and the second compartment are disconnected.

In certain embodiments, the first drug content is the same as the second drug content. In certain embodiments, the first drug content is different from the second drug content.

In certain embodiments, the first compartment has a first aperture that is covered by a first plug, and the second compartment has a second aperture that is covered by a second plug. In certain embodiments, the first plug is more permeable than the second plug. In certain embodiments, the first plug erodes faster than the second plug.

In certain embodiments, the first compartment is enclosed by a first wall, and the second compartment is enclosed by a second wall.

In certain embodiments, the first wall is thicker than the second wall. In certain embodiments, the first wall is more permeable than the second wall. In certain embodiments, the first wall erodes faster than the second wall.

DETAILED DESCRIPTION OF THE INVENTION

Figure 1A:
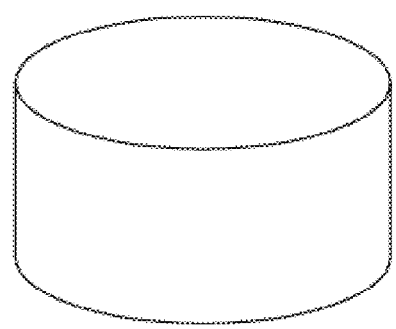
FIG. 1A shows a conventional dosage form comprising a drug content.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. In this disclosure, when a range is given as "(a first number) to (a second number)" or "(a first number)-(a second number)," this means a range whose lower limit is the first number and whose upper limit is the second number. For example, 2 to 10 millimeters means a range whose lower limit is 2 millimeters, and whose upper limit is 10 millimeters.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without these specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Controlled Release Dosage Form

Figure 1B:
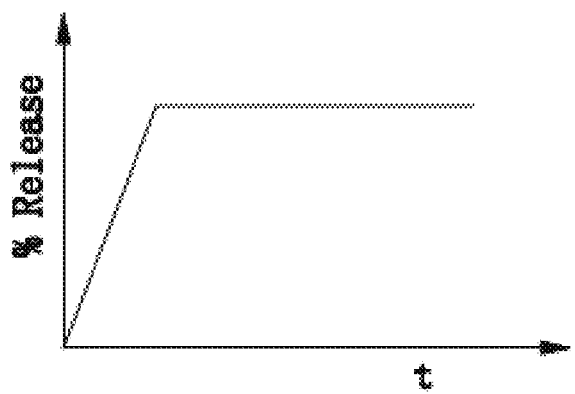
FIG. 1B illustrates the release profile of the dosage form of FIG. 1A when administered to a subject.
Figure 1C:
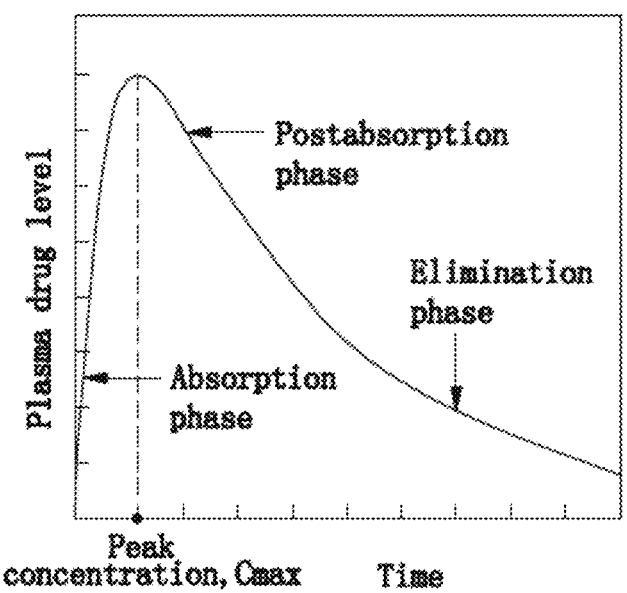
FIG. 1C shows the plasma drug level when the dosage form of FIG. 1A is administered to a subject.
Figure 1D:
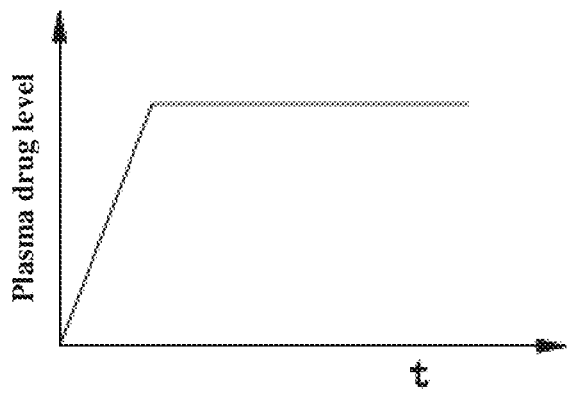
FIG. 1D shows the plasma drug level of a controlled release dosage form having the zero-order drug release profile when administered to a subject.

Conventional solid dosage forms, e.g., compressed tablets, are composed of a substrate where active drug ingredient is dissolved or embedded (FIG. 1A). Currently conventional solid dosage forms exhibit first-order drug release profile (FIG. 1B) where the plasma level of the drug increases rapidly to an extremely high level after administration and then decreases exponentially (see FIG. 1C). This poses disadvantages such as minimal therapeutic efficacy due to reduced drug levels or drug toxicity which can occur at high concentrations. This type of drug release does not allow for appropriate plasma drug level balance. The instant invention relates to modified or controlled release oral drug delivery system, which offers advantages over conventional systems, including increased patient compliance, selective pharmacological action, reduced side effects and reduced dosing frequency. Controlled release offers prolonged delivery of drugs and maintenance of plasma levels within a therapeutic range. For example, a drug delivery system exhibiting zero-order drug release profile (FIG. 1D) allows for a constant quantity of drug to be release over an extended period of time, resulting in uniform and sustained drug delivery. As a result, zero-order release profile may be desired in antibiotic delivery, the treatment of hypertension, pain management, antidepressant delivery and numerous other conditions that require constant plasma drug levels.

Therefore, one aspect of the present disclosure provides a stable solid pharmaceutical dosage form for oral administration, which has a controlled release profile. In certain embodiments, the dosage form includes a substrate forming at least one compartment and a drug content loaded into the compartment. The dosage form is so designed that the release of the active pharmaceutical ingredient of the drug content can be controlled, e.g., by opening the compartment in a predetermined manner.

A. Substrate

As used herein, "substrate" refers to a structure in which a drug is enclosed or embedded. The substrate of a dosage form of the instant invention can be of any size and shape that are suitable for oral administration. In certain embodiments, the substrate is a flat round tablet having a diameter of around 2 mm, 3 mm, 4 mm, 5 mm, 6 mm, 7 mm, 8 mm, 9 mm, 10 mm, 11 mm 12 mm. In certain embodiments, the substrate is an oval tablet having a dimension of around a mm×b mm, wherein a is 5 to 15 and b is 2 to 10. In certain embodiments, the substrate has a capsule shape.

In certain embodiments, the substrate is made of a hydrophilic polymer (e.g., hydroxypropylmethylcellulose (HPMC) and poly(ethylene oxide) (PEO)), a hydrophobic polymer (e.g., ethylcellulose (EC)), a swellable polymer, a non-swellable polymer, a porous polymer, a non-porous polymer, an erodible polymer, or a non-erodible polymer.

In certain embodiments, the dosage form has a monolithic substrate. In certain embodiments, the substrate consists of several pieces, each piece made of the same or different material.

In certain embodiments, the substrate is made of a thermoplastic material. As used herein, a "thermoplastic material" refers to a material having the ability to be shaped using heat and pressure. In certain embodiments, the thermoplastic materials may, for example, be hydrophilic, gel-forming materials, from which drug content release proceeds mainly by diffusion, or hydrophobic materials, from which drug content release proceeds mainly by diffusion from the pores in the substrate. Polymers, particularly cellulose ethers, cellulose esters and/or acrylic resins can be used as hydrophilic thermoplastic materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are suitable for use as thermoplastic materials. Physiologically acceptable, hydrophobic materials that are known to the person skilled in the art, such as mono- or diglycerides of C12-C30 fatty acids and/or C12-C30 fatty alcohols and/or waxes or mixtures thereof may be used as thermoplastic material. Substrate prepared from hydrophobic materials, such as hydrophobic polymers, waxes, fats, long-chain fatty acids, fatty alcohols or corresponding esters or ethers or mixtures thereof are also envisioned.

In certain embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), Polyoxyl 40 Hydrogenerated Castor Oil, Methyl cellulose (MC), Ethyl cellulose (EC), Poloxamer, hydroxypropyl methylcellulose phthalate (HPMCP), Poloxamer, Hydrogenated Castor & Soybean Oil, Glyceryl Palmitostearate, Carnauba Wax, polylactic acid (PLA), polyglycolic acid (PGA), Cellulose acetate butyrate (CAB), Colloidal Silicon, Dioxide, Sucrose, Glucose, Polyvinyl Acetate Phthalate (PVAP) and a combination thereof.

Properties and sources of various thermoplastic materials are listed in Table 1.

In certain embodiments, the thermoplastic material allows the dosage form to be made using an additive method such as fused deposition modeling (FDM). In certain embodiments, the substrate can be made by using a three-dimensional printer (3D printer) configured to extruding the thermoplastic material. Typically, the thermoplastic material is melted in the 3D printer before being extruded to form the substrate. In certain embodiment, appropriate extruders include without limitation, single or twin screw extruders with the temperature within the extruder at a range from 50° C. to 180° C. and from 80° to 140° C. In general, the extrusion process can be conducted at temperatures 10° to 40° C. above the glass transition (Tg) of the thermoplastic material. Once at a suitable temperature for use in the three-dimensional printer, the thermoplastic material can be deposited to the three-dimensional printing surface. The shape and size of the substrate and the compartment fabricated by the thermoplastic material can be controlled by programing the three-dimensional printing process.

In certain embodiments, the material of the substrate can be so selected to control the release profile of a drug. For example, the substrate is made of a material having desired erosion/dissolution rate, permeation rate so that when administered the compartment can be opened in a predetermined manner, and the drug content is release from the compartment at desired rate. In certain embodiments, the substrate is erodible or dissolvable and is embedded with an active pharmaceutical ingredient (API). The API is released when the substrate is eroded or dissolved The release of the drug content can also be controlled by adjusting the thickness of the substrate. For example, the substrate forming a compartment is made of a soluble material. The opening of the compartment, thus the release of the drug content loaded within can be controlled by adjusting the thickness of the walls that enclose the compartment. The thicker the wall, the slower the compartment is open, and the later the drug content is released.

B. Compartment

In certain embodiment, the dosage form disclosed herein contains at least one compartment within the substrate. As used herein, "compartment" refers to a space, part or room marked or partitioned off by the substrate. A compartment can be closed or be open (e.g., having an aperture or a passageway). A compartment can be of any geometry suitable for loading drug contents. In certain embodiments, the compartment has a shape selected from the group consisting of a pie shape, a cone shape, a pyramid shape, a cylindrical shape, a cubic or cuboidal shape, a triangular or polygonal prism shape, a tetrahedron and a combination thereof.

Figure 2A:
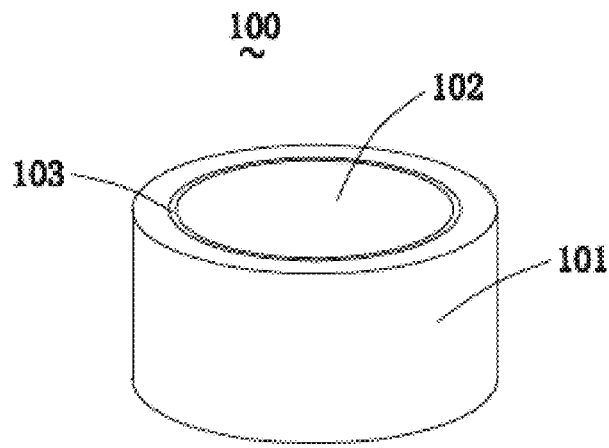
FIG. 2A shows an exemplary dosage form having a substrate that forms a compartment with a drug content loaded into the compartment.
Figure 2B:
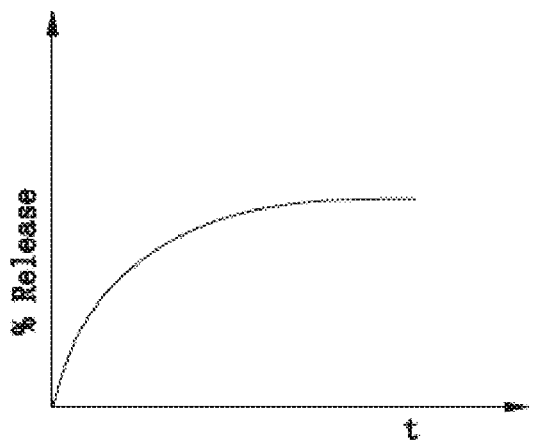
FIG. 2B shows the release of the API from the dosage form illustrated in FIG. 2A.

In certain embodiments, containing a compartment in the dosage form can increase its retention in the gastro intestinal tract. FIG. 2A illustrates an exemplary dosage form having a substrate forming a compartment where drug content is loaded. Referring to FIG. 2A, a dosage form 100 has a compartment 102 formed by a substrate 101. A drug content 103 is loaded in the compartment 102 by linking to the internal wall of the compartment 102. The compartment 102 can provide a floating effect to the dosage form and thereby extend its residence time in the stomach or in an aqueous or acidic environment. The residency time can be a function of the erosion/dissolution rate of the materials of the substrate and result in a sustained release of API as shown in FIG. 2B.

Figure 3:
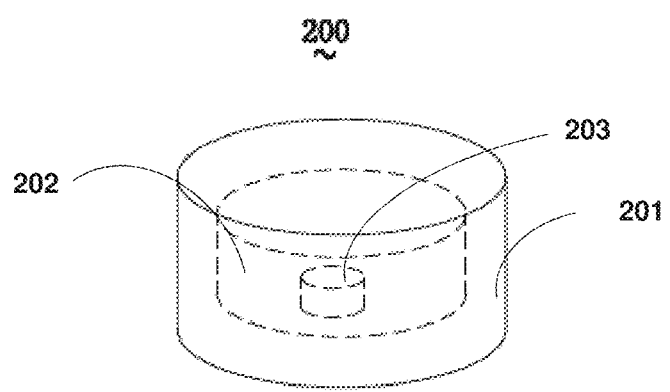
FIG. 3 shows an exemplary dosage form having a substrate that forms a compartment with another dosage form loaded into the compartment.

FIG. 3 illustrates another exemplary dosage form with increased residence in the gastro intestinal tract. Referring to FIG. 3, a dosage form 200 has a configuration that the compartment 202 contains a second dosage form 203 (e.g., a tablet) freely moving within the compartment 202. The gastro intestinal residence time of a dosage form is limited. Using floating systems can allow the dosage form to stay in stomach and continuously release the drug at the upper part of GI tract and maximize the absorption in small intestine.

In certain embodiments, the shape of the compartment is uniquely created so that the drug content can be released at a controlled rate. In certain embodiments, the compartment has a shape selected from the group consisting of a wedge shape, a pie shape, a cone shape, a pyramid shape, a cylindrical shape, a cubic or cuboidal shape, a triangular or polygonal prism shape, a tetrahedron and a combination thereof.

Figure 4A:
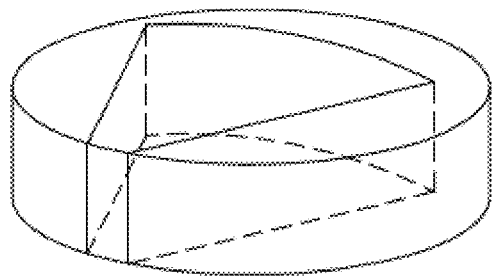
FIG. 4A shows an exemplary dosage form having a substrate forming a compartment of pie shape.
Figure 4B:
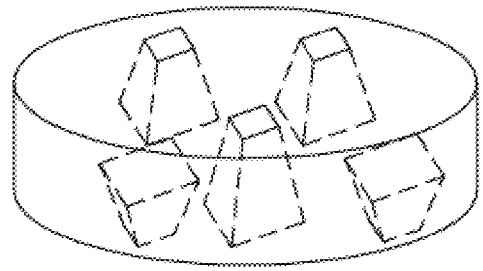
FIG. 4B shows an exemplary dosage form having a substrate forming multiple compartments containing various sized openings.
Figure 4C:
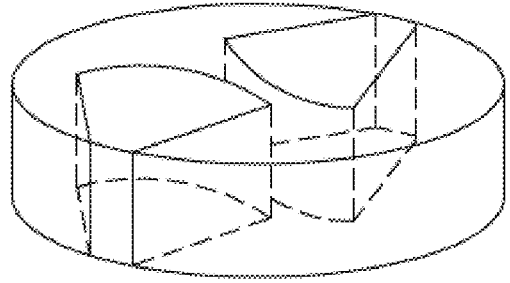
FIG. 4C shows an exemplary dosage form having a substrate forming an angled compartment.
Figure 4D:
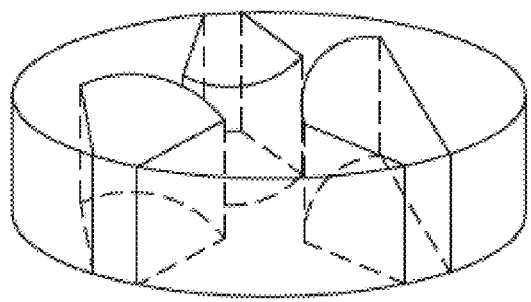
FIG. 4D shows an exemplary dosage form having a substrate forming multiple compartments of different sized radius.
Figure 4E:
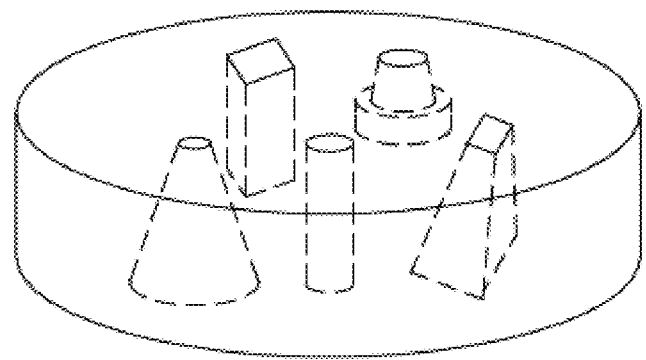
FIG. 4E shows an exemplary dosage form having a substrate forming multiple compartments of different geometric-shape that can be used to modulate release rate of the API.

In one embodiment, the compartment of the dosage form has different geometric shape. FIG. 4A shows an exemplary dosage form having a substrate forming a compartment of pie shape. FIG. 4B shows an exemplary dosage form having a substrate forming multiple compartments containing various sized openings. FIG. 4C shows an exemplary dosage form having a substrate forming an angled compartment. FIG. 4D shows an exemplary dosage form having a substrate forming multiple compartments of different sized radius.

Figure 5:
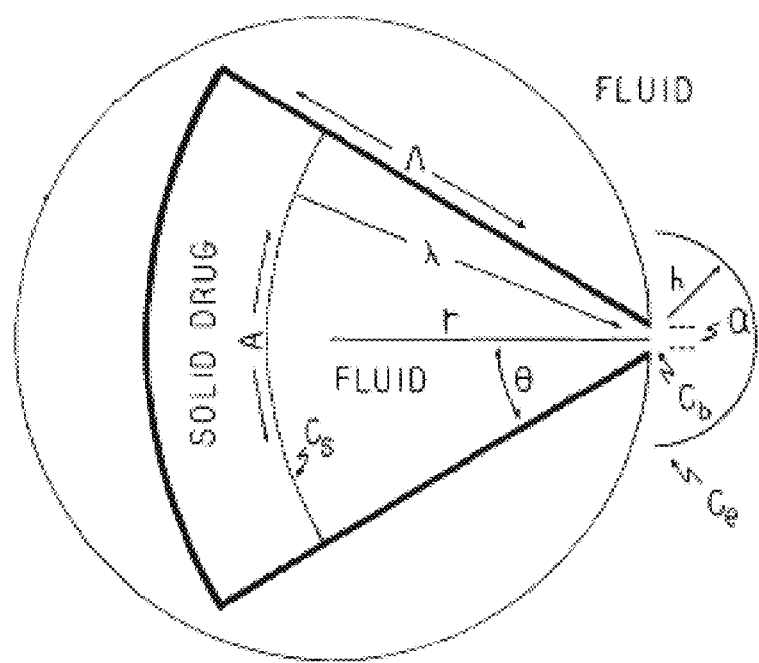
FIG. 5 shows the cross section of an exemplary dosage form having a pie-shaped compartment.

The shape of the compartment can be used to control the release profile of the dosage form. For example, R. A. Lipper and W. I. Higuichi described a delivery system that provides zero-order release profile, which is illustrated in FIG. 5. FIG. 5 shows a cross-sectional view of the delivery system having a pie-shaped compartment. The compartment communicates with the environment through a small opening. The compartment is loaded with a drug content that dissolves to release an API. The API is then released to the environment through the small opening. The dissolution rate of the drug content positively correlates to the area of the dissolution boundary of the drug content (the interface between the drug content and the space of the compartment). On the other hand, the diffusion rate of the API into the environment is negatively correlates to the diffusion path length 2. As a result, as the drug content dissolves, the area of the dissolution boundary increases, and the dissolution rate of the drug content increases. On the other hand, the diffusion path length A increases as the drug content dissolves. So the API released in the compartment needs to be transported a longer length to diffuse out of the dosage form. It is assumed that the dosage form can be so designed to provide a zero-order release kinetics (R. A. Lipper and W. I. Higuchi (1977) Analysis of theoretical behavior of a proposed zero-order drug delivery system. J. Pharm Sci 66 (2): 163-4; D. Brooke and R. J. Washkuhn (1977) Zero-order drug delivery system: theory and preliminary testing. J Pharm Sci. 66 (2): 159-162).

C. Drug Content

As used herein, the term "drug content" refers to a composition comprising one or more active ingredient, including active pharmaceutical ingredient (API), cosmetic agent, biological agent, diagnostic agent and reagent for scientific experiments.

As used herein, an API refers to an ingredient in a pharmaceutical drug that is biologically active. In certain embodiments, the API is selected from the groups consisting of local anesthetics, antiepileptic drugs and anticonvulsants, anti-Alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, anti-tuberculous drugs, antiviral drugs, antineoplasm drugs, immune-modulators, cosmetically active agents, traditional Chinese medicine (TCM) and TCM extracts.

In certain embodiments, the API is selected from the groups consisting of (R)-folitixorin, lidocaine, 11-di-deutero-ethyllinoleate, 16-dehydro-pregnenolone, 17-beta-estradiol, 2-iminobiotin, 3,5-diiodothyropropionicacid, 5-fluoro-2-deoxycytidine, 6-mercaptopurine, edotreotide, abacavir, abalone haemocyanin, abametapir, abediterol, abemaciclib, abexinostat, abiraterone, acalabrutinib, acamprosate, acamprosatecalcium, acarbose, acebilustat, aceclidine, aceclofenac, acehytisine hydrochloride, acemannan, aceneuramic acid, acetaminophen, acetylcysteine, acetylkitasamycin, acetyl-L-carnitinehydrochloride, acetylsalicylicacid, aciclovir, acipimox, acitazanolast, acitretin, aclidinium, aclidinium bromide, acolbifene, acorafloxacin, acotiamide, acrivastine, actarit, adapalene, adapalene, adefovirdipivoxil, ademetionine, adoair, afatinib, afimoxifene, afuresertib, agomelatine, aildenafilcitrate, aladorian, alalevonadifloxacin mesylate, alarelin acetate, alatrofloxacin mesylate, albendazole, albuterol sulfate, albuterpenoids, alcaftadine, aldoxorubicin, alectinib, alendronate, alendronate sodium, alendronate sodiumhydrate, alendronic acid, alfacalcidol, alfaxalone, alfentanil, alfuzosin, alisertib, aliskiren, alisporivir, alitretinoin, allantoin, allisartanisoproxil, allopurinol, almotriptan, alogliptin, alogliptin benzoate, alosetron, alpelisib, alphaketoglutarate, alphalipoic acid, alpha-lantitrypsin, alpha-cyclodextrin-stabilized sulforaphane, alprazolam, alprostadil, alprostadil alfadex, altiratinib, altretamine, altropane, aluminum sulfate, alvimopan, alvocidib, amantadine, amantadine hydrochloride, ambrisentan, ambroxol, ambroxol hydrochloride, amcasertib, amfetamine, amfetamine polistirex, amifampridine, amifampridine phosphate, amifostine, amikacin, amiloride, aminolevulinic, aminolevulinic acid, aminolevulinic acid hydrochloride, aminopterin, amiodarone, amiselimod, amisulpride, amitifadine hydrochloride, amitriptyline, amlexanox, amlodipine, amlodipine, amlodipinebesilate, amlodipine besylate, amlodipine camsylate, amlodipine maleate, amlodipine nicotinate, amlodipine orotate, ammonium lactate, amodiaquine, amorolfine, amosulalol, amoxicillin, amoxicillin hydrate, amphetamine, amphetamine aspartate, amphetamine sulfate, amphotericinB, amphotericinB cholesterylsulfate, amphotericinB lipid complex, ampicillin sodium, ampiroxicam, amrinone, amrubicin, amtolmetinguacil, anacetrapib, anagliptin, anagrelide, anamorelin, anastrozole, ancrod, androgen, andrographolide, anecortave, anidulafungin, aniracetam, anistreplase, anlotinib, antazoline, antiandrogens, antineoplaston A-10, antineoplaston AS2-1, antofloxacin hydrochloride, antroquinonol, apabetalone, apalutamide, apatinib mesylate, apaziquone, apilimod mesylate, apixaban, apomorphine, apomorphine hydrochloride, apremilast, aprepitant, apricitabine, aramchol, aranidipine, arasertaconazole, arasertaconazol enitrate, arbaclofen, arbaclofen placarbil, arbekacin, arbekacin sulfate, ardeparin sodium, arformoterol, argatroban, arhalofenate, arimoclomol, aripiprazole, aripiprazole lauroxil, armodafinil, arsenictrioxide, arsenious acid, artefenomel mesylate, artemether, artemotil, artenimol, arterolane maleate, artesunate, Artiss, asapiprant, asenapine, asimadoline, astodrimer, astragaloside, asunaprevir, ataciguat, ataluren, atazanavir, atazanavir sulfate, atenolol, atomoxetine, atorvastatin, atorvastatin calcium, atorvastatin strontium, atovaquone, atrasentan, atropine, auranofin, auriclosene, avacincaptadpegol sodium, avacopan, avanafil, avatrombopag, avibactam, avibactam sodium, AvidinOx, aviptadil, avitinib, avoralstat, axelopran, axitinib, azacitidine, azacytidine, azasetron, azelaicacid, azelastine, azelastine hydrochloride, azeliragon, azelnidipine, azilsartan, azilsartan medoxomil potassium, azilsartan trimethylethanolamine, azimilide, azithromycin, azithromycin lactobionate, aztreonam, aztreonam lysine, azvudine, baclofen, bafetinib, Baicalein, baicalin, BAK-freelatanoprost, balofloxacin, balsalazide, balsalazide sodium, bambuterol, barasertib, bardoxolone methyl, baricitinib, barnidipine, basmisanil, batefenterol succinate, bazedoxifene, beclabuvir, beclometasone dipropionate, beclomethasone dipropionate, bedaquiline, bedoradrine, belinostat, beloranib, belotecan, bempedoic acid, benapenem, benazepril, bencycloquidium bromide, bendamustine, bendamustine hydrochloride, benidipine, benserazide, bentamapimod, benzalkonium chloride, benzhydrocodone, benznidazole, benzocaine, benzoylperoxide, benzydamineHCL, bepotastine, bepotastine calciumdihydrate, bepotastine salicylate, beractant, beraprost sodium, besifloxacin, besifovir, besipirdine, beta-elemene, betahistine, betaine anhydrous, betamethasone, betamethasone butyrate propionate, betamethasonedipropionate, betamethasone valerate, betamipron, betaxolol, betaxolol hydrochloride, bethanechol, betrixaban, bevacizumab, bexagliflozin, bexarotene, bezafibrate, biafungin, biapenem, bicalutamide, bicizar, bictegravir, bicyclol, bilastine, bimatoprost, binimetinib, biotin, birabresibdihydrate, biskalcitrate potassium, bismuth subgallate, bismuthyl ecabet, bisnorcymserine, bisoprolol, bisoprolol fumarate, bitespiramycin, bixalomer, bleomycin, blonanserin, boanmycin hydrochloride, boceprevir, bortezomib, bosentan, bosentan hydrate, bosutinib, bovactant, brexpiprazole, briciclib sodium, brigatinib, brilacidin, brimapitide, brimonidine, brincidofovir, brinzolamide, brivanibalaninate, brivaracetam, brivudine, brolucizumab, bromazepam, bromfenac, bromfenac sodium, bromocriptine, bronchostat, brotizolam, bryostatin-1, bucindolol, bucladesine, budesonide, budipine, buflomedil, bulaquin, bunazosin, buparlisib, bupivacaine, bupivacaine hydrochloride, buprenorphine, buprenorphine hydrochloride, bupropion, bupropion hydrochloride, burixafor, buserelin acetate, buspirone, buspirone hydrochloride, busulfan, busulfex, butenafine, butorphanol tartrate, butylphthalide, cabazitaxel, cabergoline, cabotegravir, cabozantinib S-malate, cadazolid, cadrofloxacin, caffeine, caffeine citrate, cafnea, cafusertib hydrochloride, calcipotriol, calcitriol, calcium acetate, calciumfolinate, calcium levofolinate, calcium polycarbophil, calfactant, calmangafodipir, calsurf, camicinal, camostat mesylate, camptothecin, canagliflozin, candesartan, candesartan cilexetil, canfosfamide, cangrelor, cannabidiol, capecitabine, capmatinib, capsaicin, captopril, carbamazepine, carbetocin, carbidopa, carbinoxamine, carbocysteine, carboplatin, cardidopa, carfilzomib, carglumicacid, cariprazine, carisbamate, carmustine, carotegastmethyl, carteolol, carteolol hydrochloride, carumonam, carvedilol, carvedilolphosphate, caspofungin, catechin, cebranopadol, cediranib, cefaclor, cefadroxil, cefathiamidine, cefazolin sodium pentahydrate, cefcapene, cefdinir, cefditorenpivoxil, cefepime, cefepime dihydrochloride, cefetametpivoxil hydrochloride, cefiderocol, cefilavancin, cefminox, cefoperazone, cefoperazone sodium, cefoselis, cefotaxime, cefotaxime sodium, cefotiam, cefozopran, cefpirome, cefpodoxime, cefprozil, ceftaroline, ceftaroline fosamil, ceftazidime, ceftibuten, ceftobiprole medocaril, ceftolozane sulfate, ceftriaxone, ceftriaxone sodium, cefuroxime, cefuroxime sodium, celecoxib, celgosivir, celiprolol, cellprotect, cenestin, cenicriviroc, censavudine, centanafadine, cephalosporin, ceralifimod, cerdulatinib, ceritinib, ceriumnitrate, cetilistat, cetirizine, cetraxate, cevimeline, chenodeoxycholic acid, chlocibutamine, chlorhexidine, chlormadinone acetate, chlorogenicacid, chloroquine, chloroxoquinoline, chlorpheniramine, chlorpheniramine maleate, chlorpheniramine polistirex, chlortalidone, chlorthalidone, cholecalciferol, cholic acid, choline alfoscerate, choline diepalrestat, choline fenofibrate, ciclesonide, ciclopiroxolamine, ciclosporin, cidofovir, cidoxepin, cilastatin, cilazapril, cilnidipine, cilostazol, cimetidine, cinacalcet, cinepazide maleate, cinhyaluronate sodium, cinitapride tartrate, cipargamin, ciprofibrate, ciprofloxacin, ciprofloxacin hydrochloride, ciraparantag, circadin, cisatracurium besilate, cisplatin, citalopram, citalopram hydrobromide, citicoline, citrulline, cladribine, clarithromycin, clavulanate potassium, clavulanic acid, clazosentan, clevidipine, clevudine, clindamycin, clindamycin hydrochloride, clindamycin phosphate, clioquinol, clobazam, clobetasolpropionate, clobetasolpropionatefoam, clodronic acid, clofarabine, clofazimine, clomipramine, clomipramine hydrochloride, clonazepam, clonidine, clonidine hydrochloride, clopidogrel, clopidogrel besylate, clopidogrel bisulfate, clopidogrel camsylate, clopidogrel hydrogensulfate, clopidogrel napadisilate, clopidogrel resinate, clotrimazole, clozapine, cobamamide, cobicistat, cobimetinib, cobiprostone, codeine, codeine polistirex, colchicine, colecalciferol, colesevelam, colestilan, colforsin daropate, colfosceril palmitate, colistimethate sodium, conivaptan, copanlisib, copperhistidine, cortexolone 17alpha-propionate, cositecan, crenolanib, cridanimod sodium, crisaborole, crizotinib, crofelemer, crolibulin, cromoglicic acid, cromolyn sodium, cutamesine dihydrochloride, cyanocobalamin, cyclizine lactate, cyclobenzaprine hydrochloride, cyclophosphamide, cyclophosphamide monohydrate, cyclosporin, cyproterone, cyproterone acetate, cytarabine, cytarabine ocfosfate, dabigatran etexilate, dabrafenib, daclatasvir, dacomitinib, dalbavancin, dalcetrapib, dalfampridine, dalfopristin, dalteparin sodium, danaparoid sodium, danazol, danirixin, danoprevir, dantrolene sodium, danusertib, dapaconazole, dapagliflozin, dapagliflozin propanediol, dapirazole, dapivirine, dapoxetine, daprodustat, dapsone, darifenacin, darinaparsin, darunavir, dasabuvir, dasatinib, dasotraline, daunorubicin, decitabine, decuprate, defactinib, deferasirox, deferiprone, deferoxamine mesylate, deflazacort, deflexifol, delafloxacin, delamanid, delapril, delapril hydrochloride, delavirdine, denibulin, deoxyandrographolide, dermatansulfate, desflurane, desipramine hydrochloride, desloratadine, desmopressin, desmopressin acetate, desogestrel, desonide, desvenlafaxine, deudextromethorphan hydrobromide, deuteporfin, deuterated levodopa, deuteratedvenlafaxine, deutetrabenazine, dexamethasone, dexamethasone acetate, dexamethasone cipecilate, dexamethasone palmitate, dexamethasone sodiumphosphate, dexamfetamine, dexanabinol, dexferrum, dexketoprofen trometamol, dexlansoprazole, dexmedetomidine, dexmethylphenidate, dexpramipexole, dexrazoxane, dexsotalol, dextroamphetamine saccharate, dextroamphetamine sulfate, dextromethorphan, dextromethorphan hydrobromide, dextropropoxyphene, diacerein, diamorphine hydrochloride, dianhydrogalactitol, diazepam, diazoxidecholine, diclofenac, diclofenac potassium, diclofenac sodium, diclofenamide, dicycloplatin, didanosine, dienogest, difluprednate, digoxin, dihomogamma-linolenic acid, dihydroergocristine, dihydroergotamine, dihydroergotamine mesylate, diltiazem, diltiazem hydrochloride, dimesna, dimethyl fumarate, dimiracetam, dinoprostone, diphenylcyclopropenone, dipraglurant, dipyridamole, diquafosoltetra sodium, dirithromycin, disufenton sodium, disulfiram, dithranol, d-methadone, docarpamine, docetaxel, dociparstat, docosanol, dofetilide, dolasetron, dolutegravir, domperidone, donafenib tosylate, donepezil, donepezil hydrochloride, dopamine, doravirine, doripenem, dorzolamide, dorzolamide hydrochloride, dosmalfate, doxacurium chloride, doxazosin, doxazosin mesylate, doxepin hydrochloride, doxercalciferol, doxifluridine, doxofylline, doxorubicin, doxorubicin hydrochloride, doxycycline, doxycycline hyclate, doxylamine succinate, dronabinol, dronedarone, drospirenone, droxidopa, D-tagatose, duloxetine, duloxetine hydrochloride, dutasteride, duvelisib, ebastine, eberconazole, ebselen, ecabet, econazolenitrate, ecopipam, edaravone, edivoxetine, edonerpic maleate, edoxaban, efatutazone, efavirenz, efinaconazole, eflornithine, efonidipin hydrochloride, egualen sodium, eicosapentaenoic acid monoglycerides, elafibranor, elagolix, elamipretide, elbasvir, eldecalcitol, eleclazine, elesclomol sodium, eletriptan, eliglustattartrate, elobixibat, eltrombopag, eluxadoline dihydrochloride, elvitegravir, emdogain, emedastine, emeramide, emixustat, emodepside, empagliflozin, emricasan, emtricitabine, enalapril, enalaprilmaleate, enasidenib, encenicline, enclomifene citrate, encorafenib, endoxifen, enobosarm, enoxacin gluconate, enoxaparin sodium, enprostil, entacapone, entasobulin, entecavir, entecavir maleate, entinostat, entospletinib, entrectinib, enzalutamide, enzastaurin, epacadostat, epalrestat, eperisone, epetraborole, ephedrine sulfate, epinastine hydrochloride, epinephrine, epirubicin, epirubicin hydrochloride, episalvan, epitinib, eplerenone, epoprostenol, episteride, eprodisate, eprosartan, eptaplatin, eravacycline, erdafitinib, erdosteine, eribulin mesylate, erlotinib, ertapenem, erteberel, ertugliflozin, erythromycin, erythromycin acistrate, erythromycin stinoprate, escitalopram, esketamine, esketamine hydrochloride, eslicarbazepine acetate, esmolol hydrochloride, esomeprazole, esomeprazole magnesium, esomeprazole strontium, esomeprazole, estetrol, estradiol, estradiol acetate, estradiol cypionate, estradiol valerate, estrodiol, estrogen, esuberaprost sodium, eszopiclone, etamicastat, ethambutol hydrochloride, ethaselen, ethinylestradiol, ethylhydrogenfumarate calcium, ethylhydrogenfumarate magnesium, ethylhydrogenfumara tezinc, ethynylestradiol, etidronicacid, etimicin sulfate, etirinotecanpegol, etizolam, etodolac, etonogestrel, etoposide, etoposide phosphate, etoricoxib, etravirine, etripamil, eupatilin, evenamide hydrochloride, everolimus, evofosfamide, evogliptin, exemestane, exendin (9-39), exeporfinium chloride, ezatiostat, ezetimibe, ezutromid, fadolmidine, fadrozole, faldaprevir, falecalcitriol, famciclovir, famitinib, famotidine, fampridine, faropenem, fasitibant chloride, fasoracetam, fasudil, fasudil hydrochloride, fasudil mesylate, favipiravir, febarbamate, febuxostat, fedovapagon, felbamate, felbinac trometamol, felodipine, femitra, fenfluramine hydrochloride, fenobam, fenofibrate, fenofibric acid, fenoldopam, fenoterol, fenretinide, fentanyl, fentanyl citrate, fenticonazole, fermagate, ferriccitrate, ferricmaltol, ferumoxytol, fesoterodine fumarate, fevipiprant, fexinidazole, fexofenadine, fibrinsealant, fibrinogen, fibrinogensealant, fidaxomicin, filanesib, filgotinib, filociclovir, fimaporfin, fimasartan, finafloxacin, finafloxacin hydrochloride, finasteride, finerenone, fingolimod, fipamezole, firtecanpegol, flecainide, fleroxacin, flibanserin, flomoxef, floxuridine, fluazolepali, fluconazole, fludarabine, flumatinib, flumazenil, flunisolide, fluocinolone acetonide, fluocinonide, fluorapacin, fluorouracil, fluoxetine, fluoxetine hydrochloride, flupirtine, flurbiprofen, flurbiprofenaxetil, flurbiprofen sodium, flurithromycin, fluticasone, fluticasone furoate, fluticasone propionate, flutrimazole, fluvastatin, fluvoxamine, folic acid, folinate, foliumginkgo, fomepizole, fonadelpar, fondaparinux sodium, foretinib, formestane, formoterol, formoterol fumarate, forodesine, fosamprenavir, fosaprepitant, fosbretabulin, fosbretabulin disodium, fosfluconazole, fosfomycin, fosfomycindi sodium, fosfomycintrometamol, fosinopril, fosinopril sodium, fosmidomycin, fosphenytoin, fospropofol, fosravuconazole, fostamatinib, fostemsavir trometamine, fotagliptin benzoate, fotemustine, frovatriptan, fruquintinib, fudosteine, fulvestrant, funapide, furosemide, fusidic acid, gabapentin, gabapentinenacarbil, gabexate mesylate, gacyclidine, gadobutrol, gadoversetamide, gadoxetate disodium, galantamine, galeterone, galidesivir, gallium nitrate, galunisertib, gambogic acid, ganaxolone, ganciclovir, ganetespib, ganirelix acetate, garenoxacin, gatifloxacin, gatifloxacin mesylate, gedatolisib, gefitinib, gemcabene, gemcitabine, gemcitabine hydrochloride, gemfibrozil, gemifloxacin, gemigliptin, gemigliptintartaric acid, genistein, gentamicin, gentiopicrin, gepirone, gepotidacin, gestodene, gestrinone, timolol maleate, gilteritinib, gimeracil, ginsenosideC-K, ginsenosideRg3, givinostat, glasdegib, glatiramer acetate, glecaprevir, glesatinib glycolate, glibenclamide, gliclazide, glimepiride, glipizide, glufosfamide, glutamine, glutathionarsenoxide, glycerol phenylbutyrate, glycopyrronium, glycopyrronium bromide, glycopyrronium tosylate, glycyrrhizi cacid, ganglioside, golotimod, gosogliptin, granisetron, granisetron hydrochloride, grazoprevir, guaifenesin, guaimesal, guanfacine, gusperimus trihydrochloride, haemophilusinfluenzae, halobetasol propionate, halofantrine, halometasone, healon, hematoporphyrin, hemearginate, hemocoagulase *acutus*, heparin, Herbiron, hetrombopag, hextend, higenaminehydrochloride, histamine dihydrochloride, HPPHphotosensitizer, humanapotransferrin, humanplasminogen, huperzineA, hyaluronate sodium, hydralazine, hydrochloride, hydrochlorothiazide, hydrocodone, hydrocodone bitartrate, hydrocodone polistirex, hydrocortisone, hydrogenperoxide, hydromorphone, hydromorphone hydrochloride, hydroxocobalamin, hydroxycarbamide, hydroxychloroquine, hydroxyprogesterone caproate, hydroxysafflor yellowA, hylastan, hypericin, hypoestoxide, ibandronate, ibandronic acid, iberogastN, ibodutant, ibrutinib, ibudilast, ibuprofen, ibutilide, ibutilide fumarate, icaritin, iclaprim, icosabutate, icosapent, icosapentethyl, icosapentethylester, icotinib hydrochloride, idalopirdine, idasanutlin, idebenone, idelalisib, idoxuridine, idronoxil, ifetroban, ifetrobansodium, iguratimod, ilansoprazole, ilaprazole, iloperidone, iloprost, iloprostbetadexclathrate, imatinib, imatinibmesylate, imeglimin, imidafenacin, imidapril, imidazole salicylate, imidol hydrochloride, imigliptin dihydrochloride, imipenem, imiquimod, imisopasem manganese, imrecoxib, incadronic acid, incobotulinumtoxin, indacaterol, indacaterol maleate, indapamide, indeloxazine, Indimitecan, indinavir, indisetron, indometacin, indoramin, indotecan, indoximod, inecalcitol, infigratinib, Ingavirin, ingenolmebutate, inhaled sodium nitrite, ferric carboxymaltose, inosine, intepirdine, iodiconazole, ipatasertib dihydrochloride, ipragliflozin, ipratropium, ipratropium bromide, iptakalim, irbesartan, irinotecan, irinotecan hydrochloride, irinotecan sucrosofate, irofulven, iron isomaltoside1000, iron protein succinylate, irosustat, isogladine maleate, isavuconazonium chloride/sulfate, isodibut, isoflurane, isoniazid, isopropylunoprostone, isosorbidedi nitrate, isosorbide mononitrate, isosteviol, isothiafludine, isotretinoin, isradipine, istaroxime, istradefylline, itacitinib, itopride hydrochloride, itraconazole, ivabradine hemisulfate, ivabradine hydrochloride, ivacaftor, ivermectin, ivosidenib, aflibercept, ixabepilone, ixazomib citrate, kallikrein, kangbeide, ketamine, ketanserin, ketoconazole, ketoprofen, ketorolac, ketorolac tromethamine, ketotifen, kevetrin, kukoamine Bmesylate, L-4-chlorokynurenine, lacidipine, lacosamide, lactitol, ladarixin, ladostigil, laflunimus, lafutidine, lamivudine, lamotrigine, landiolol, landiolol hydrochloride, laninamivir octanoate, lanoconazole, lansoprazole, lanthanum carbonate, lapatinib, laquinimod, laromustine, lasmiditan, lasofoxifene, latanoprost, latanoprostenebunod, lauflumide, ledipasvir, lefamulin, leflunomide, lemborexant, lenalidomide, lentinan, lentinansulfate, lentinanviral, lenvatinib mesylate, lercanidipine, lesinurad, leteprinim, letermovir, letrozole, leucine, leuprorelin acetate, levalbuterol, levalbuterol hydrochloride, levamisole, levamlodipine, levamlodipine besylate, levamlodipine maleate, levetiracetam, levobupivacaine, levocabastine, levocabastine hydrochloride, levocarnitine, levocetirizine dihydrochloride, levodopa, levodoxazosin mesylate, levofloxacin, levoketoconazole, levomilnacipran, levonadifloxacin arginine salt, levonorgestrel, levonorgestrel butanoate, levo-phencynonate hydrochloride, levornidazole, levorphanol, levosimendan, levothyroxine sodium, levotuss, L-glutamine, lidocaine, lifitegrast, ligustrazine hydrochloride, limaprost, linagliptin, linezolid, liothyronine, liothyronine sodium, lipobean, liposomal curcumin, lipoteichoic acid, liranaftate, lisdexamfetamine, lisinopril, lisofylline, lisuridehydrogen maleate, lithiumcitrate, lithiumsuccinate, lixivaptan, lobaplatin, lobeglitazone, lodenafil carbonate, lofexidine, lomefloxacin, lomerizine, lomerizine dihydrochloride, lomitapide, lonafarnib, lonidamine, loperamide, loperamideoxide, lopinavir, loratadine, lorazepam, lorcaserin, lorediplon, lorlatinib, L-ornithineL-aspartate, lornoxicam, losartan, losartan potassium, losmapimod, loteprednoletabonate, lovastatin, loxapine, loxoprofen, L-praziquantel, lubiprostone, lucanthone, lucerastat, lucinactant, lucitanib hydrochloride, luliconazole, lumacaftor, lumateperone toluene sulfonate, lumefantrine, lumiracoxib, lunacalcipol, lurasidone, lurbinectedin, luseogliflozin hydrate, lusutrombopag, lysine acetylsalicylate, macimorelin, macitentan, mafenide, magnesium carbonate, magnesium isoglycyrrhizinate, mangafodipir, manidipine, manidipine dihydrochloride, mannitol, maraviroc, maribavir, marizomib, masilukast, masitinib, mavoglurant, maxacalcitol, mebendazole, mebiphon, mecamylamine, mecamylamine hydrochloride, mechlorethamine, mecobalamin, medroxyprogesterone, medroxyprogesteroneacetate, mefloquine, megestrol, megestrolacetate, meisuoshuli, melevodopa, meloxicam, melphalan, melphalanflufenamide hydrochloride, memantine, memantine hydrochloride, menadione sodium bisulfite, menatetrenone, mepacrine, mequinol, mercaptamine, mercaptamine bitartrate, mercaptamine hydrochloride, mercaptopurine, merestinib, meropenem, merotocin, mesalamine, mesalazine, metacavir, metadoxine, metamizolesodium, metaxalone, metergoline, metformin, metformin hydrochloride, methadone, methazolamide, methotrexate, methoxyflurane, methylaminolevulinate hydrochloride, methylnaltrexone bromide, methylnaltrexone, methylphenidate, methylphenidate hydrochloride, methylprednisolone, methylprednisolone aceponate, methylthioninium chloride, metirosine, metoclopramide, metoprolol, metoprolol succinate, metrifonate, metronidazole, metyrapone, mexiletine, mibefradil, miconazole, miconazole nitrate, midazolam, midazolam hydrochloride, midodrine, midostaurin, mifamurtide, mifepristone, migalastat, miglitol, miglustat, milnacipran, milrinone, miltefosine, minaprine, minocycline, minocycline hydrochloride, minodronic acid, minoxidil, mirabegron, miriplatin hydrate, mirodenafil, mirodenafil hydrochloride, mirogabalin, mirtazapine, misoprostol, mitiglinide, mitomycin, mitoxantrone, mitoxantrone hydrochloride, mivotilate, mizolastine, mizoribine, mocetinostat dihydrobromide, moclobemide, modafinil, doxycycline, modipafant, moexipril, mofezolac, molidustat, molindone hydrochloride, momelotinib, mometasone, monepantel, monoammonium glycyrrhizinate, monobenzone, monosodium alphaluminol, monoterpene perillyl alcohol, montelukast, montelukast sodium, montmorillonite, moracizine, morinidazole, morphine, morphine glucuronide, morphine pitavastatin, morphine sulfate, morphothiadine mesilate, mosapride, motolimod, moxidectin, moxifloxacin, moxifloxacin hydochloride, moxonidine, moxonidine hydrochloride, mozavaptan, muparfostat sodium, mupirocin, mycobactovir, mycophenolatemofetil, myristylnicotinate, nabilone, nabiximols, nabumetone, N-acetylcysteine, nacystelyn, nadifloxacin, nadolol, nadroparin calcium, naftifine hydrochloride, naftopidil, nalbuphine, nalbuphine sebacate, naldemedine, nalfurafine, nalmefene, naloxegol, naloxone, naloxone hydrochloride, naltrexone, naltrexone hydrochloride, naluzotan, nandrolone decanoate, napabucasin, naphazoline, naphthoquine, naproxen, naproxen sodium, naquotinib mesylate, naratriptan, narlaprevir, nasapaque, nasaruplase, nastorazepide calcium, nateglinide, navamepent, nazartinib, nebivolol, necuparanib, nedaplatin, nedocromil, nelarabine, nelfinavir, nelotanserin, nemonapride, nemonoxacin, neoandrographolide, neosaxitoxin, neostigmine methylsulfate, nepadutant, nepafenac, nepicastat, nepolong, neramexane, neratinib, neridronic acid, netarsudil, netilmicin, netupitant, nevirapine, niacin, nicardipine, nicergoline, nicorandil, nicotiflorin, nicotine, nicotinicacid, nicousamide, nifedipine, nifekalant, nifeviroc, Nifurtimox, nifurzide, nikkomycin, nilotinib, nilutamide, nilvadipine, nimesulide, nimodipine, nimorazole, ningetinib, nintedanib, niraparib, nisoldipine, nitazoxanide, nitisinone, nitrendipine, nitricoxide, nitroglycerin, nitroglycerine, nizatidine, nokxaban, nolatrexed, nomegestrol acetate, norelgestromin, norepinephrine, norethindrone, norethindrone acetate, norethindrone enantate, norethisterone, norethisterone acetate, norfloxacin, norgestimate, noribogaine, norursodeoxycholic acid, obeticholicacid, octenidine, octohydroaminoacridine succinate, octreotide, octreotide hydrochloride, odalasvir, odanacatib, odiparcil, ofloxacin, olanzapine, olaparib, olesoxime, oliceridine, olmesartan, olmesartan cilexetil, olmesartan medoxomil, olodaterol, olodaterol hydrochloride, olopatadine, olopatadine hydrochloride, olprinone, olsalazine, oltipraz, omacetaxine mepesuccinate, omadacycline, omarigliptin, omaveloxolone, ombitasvir, omecamtivmecarbil, omega-3carboxylicacids, omeprazole, omigapil, omoconazole, onalespib, onapristone, ondansetron, ondelopran, opicapone, opipramol, methylphenidate, orcinoside, orilotimod, oritavancin, orlistat, ornithine phenylacetate, ornoprostil, ortataxel, orteronel, orthovisc, orvepitant, oseltamivir, osilodrostat, osimertinib, Osiris Phleum pratense, ospemifene, oteracil potassium, oteseconazole, oxaliplatin, oxaloacetic acid, oxandrolone, oxazepam, oxcarbazepine, oxfendazole, oxidizedglutathione sodium, oxiracetam, oxybutynin, oxybutynin hydrochloride, oxycodone, oxycodone hydrochloride, oxymetazoline, oxymetazoline hydrochloride, oxymorphone, oxytocin, ozagrel, ozagrel hydrochloride, ozagrelsodium, ozanimod, ozenoxacin, paclitaxel, paclitaxel poliglumex, pacritinib, palbociclib, paliperidone, paliperidone palmitate, palmidrol, palonosetron, palovarotene, pamidronate disodium, pancrelipase, panipenem, panobinostat, pantoprazole, paracetamol, parecoxib, paricalcitol, paritaprevir, parnaparin sodium, parogrelil, paromomycin, paroxetine, paroxetine hydrochloride hemihydrate, paroxetine mesylate, patiromer calcium, patupilone, pazopanib, pazufloxacin, pazufloxacin mesylate, pefcalcitol, peficitinib, pegylatedapo-filgrastim, pelubiprofen, pemafibrate, pemetrexed disodium, pemirolast, pemirolast potassium, pemirolast sodium, penciclovir, penehyclidine hydrochloride, pentamidine, pentetate calcium trisodium, pentetatezinc trisodium, pentetrazol, pentosan polysulfate sodium, pentostatin, pentoxifylline, peramivir, perampanel, perchlozone, peretinoin, perflenapent, perflubronemulsion, perfluorooctyl bromide, pergolide, perhexiline maleate, perifosine, perindopril, perindopril arginine, perospirone, pevonedistat, pexidartinib, PhagoBioDerm, phenchlobenpyrrone, phenethyl isothiocyanate, phenoxybenzamine hydrochloride, phentermine, phentermine hydrochloride, phentolamine mesylate, phenylbutyrate, phenylephrine, phenylephrine hydrochloride, phenytoin, phosphazid, pibrentasvir, picibanil, picroliv, picropodophyllin, pidotimod, pilocarpine, pilocarpine hydrochloride, pilsicainide, pimasertib hydrochloride, pimavanserin, pimecrolimus, pimobendan, pinocembrin, pinometostat, pioglitazone, pioglitazone hydrochloride, pipamperone, pipecuronium, piperacillin, piperacillin sodium, piperaquine, piperaquine phosphate, piperidone hydrochloridum, piperine, piperphentonamine, piracetam, pirarubicin, pirfenidone, pirmenol, piromelatine, pirotinib, piroxicam, piroxicambetadex, pitavastatin, pitavastatin calcium, pitolisant, pixantrone, plazomicin, pleconaril, plerixafor, plinabulin, pocapavir, hydromorphone, podofilox, polaprezinc, polmacoxib, polydatin, polyoxidonium, pomaglumetad methionil, pomalidomide, ponatinib, ponesimod, porfimer sodium, posaconazole, posiphen, potassium bicarbonate, potassium citrate, potassium clavulanate, poziotinib, pracinostat, pradefovir, pralatrexate, pramipexole, pramiracetam, pranlukast, pranlukast hydrate, prasterone, prasugrel, pravastatin, prazosin, prednimustine, prednisolone, prednisoloneacetate, prednisolone sodiumphosphate, prednisone, pregabalin, prempro, presatovir, pretomanid, previdersin, prexasertib, pridopidine, prilocaine, pritelivir, procaterol hydrochloride, prochlorperazine, prochlorperazinemaleate, profezyme, progesterone, progestogen, progestogendienogest, proguanil, promethazine, promitil, propafenone, propagermanium, propofol, propranolol, propranolol hydrochloride, prostat, proxodolol, prucalopride, prulifloxacin, prurisol, prussianblueinsoluble, pseudoephedrine, pseudoephedrine hydrochloride, puerarin, puquitinib mesylate, pyrazinamide, pyridoxamine dihydrochloride, pyridoxine hydrochloride, pyrimethamine, pyronaridine, pyrroltinibmaleate, quazepam, quetiapine fumarate, quetiapine, quinagolide hydrochloride, quinapril hydrochloride, quinidine sulfate, quinine sulfate, quinupristin, quisinostat, quizartinibdi hydrochloride, rabeprazole, rabeprazolesodium, rabeximod, racecadotril, radezolid, radotinib, ralfinamide, ralimetinib, ralinepag, raloxifene, raltegravir, raltitrexed, ramatroban, ramelteon, ramipril, ramosetron, ranitidine, ranitidine bismuth citrate, ranolazine, rasagiline, ravidasvir hydrochloride, raxatrigine, rebamipide, rebastinib, reboxetine, reboxetine mesylate, recilisib sodium, recoflavone, redaporfin, ibuprofen, naproxen, glycopyrronium bromide, refametinib, regorafenib, relebactam, relenopride, relugolix, remeglurant, remifentanil, remifentanil hydrochloride, remimazolam, remimazolam tosylate, remogliflozin etabonate, repaglinide, reparixin, repirinast, amlexanox, chlorcyclizine hydrochloride, bucillamine, guanabenz, mazindol, naltrexone, nitisinone, ondansetron, phacetoperane, retigabine, rosiglitazone, sodium phenylbutyrate, resiniferatoxin, resiquimod, resminostat, resveratrol, retagliptin, retapamulin, retigabine, retinoicacid, retosiban, revaprazan, revefenacin, reviparin sodium, rhein, rhenium-186 etidronate, ribavirin, ribociclib, ricolinostat, ridinilazole, ridostin, rifabutin, rifampicin, rifamycin, rifapentine, rifaximin, rigosertib sodium, rilapladib, rilpivirine, rilpivirine hydrochloride, riluzole, rimantadine, rimeporide, rimexolone, riociguat, ripasudil hydrochloride hydrate, risedronate sodium, risperidone, ritonavir, rivaroxaban, rivastigmine, rivipansel sodium, rizatriptan, rizatriptan benzoate, rmulation, rociletinib, roflumilast, rokitamycin, rolapitant, romurtide, ronacaleret, roneparstat, ronopterin, ropinirole, ropinirole hydrochloride, ropivacaine, rosebengal sodium, rosiglitazone, rosiglitazone maleate, rosiglitazone sodium, rostafuroxin, rosuvastatin, rosuvastatin calcium, rotigotine, rovatirelin, roxadustat, roxithromycin, rubitecan, rucaparib phosphate, rufinamide, rufloxacin, rupatadine, ruxolitinib, S-(-)-ornidazole phosphate disodium, sabarubicin, sacubitril, safinamide, salbutamol, salbutamol sulfate, salicyclic acid, salmeterol, salmeterol xinafoate, salubrinal, salvicine, samarium (153Sm) lexidronam, samidorphan, S-amlodipine nicotinate, sapacitabine, sapropterin, sapropterin dihydrochloride, saquinavir, saracatinib, sarecycline, saroglitazar, sarpogrelate hydrochloride, savolitinib, saxagliptin, scopolamine, scorpionvenom, omega-3polyunsaturated fatty acid, secnidazole, segesterone acetate, selegiline, selegiline hydrochloride, selepressin, selexipag, seliciclib, selinexor, selisistat, selumetinib, selurampanel, sepranolone, seratrodast, serlopitant, sertaconazole, sertaconazole nitrate, sertindole, sertraline, sertraline hydrochloride, setipiprant, sevelamer carbonate, sevelamer hydrochloride, seviteronel, sevoflurane, sevuparin sodium, sibutramine maleate, sibutramine mesylate, sildenafil, sildenafil citrate, silibinin dihydrogen succinate, silmitasertib, silodosin, silver sulfadiazine, simeprevir, simmitecan hydrochloride, simotinib hydrochloride, simvastatin, sinotecan, siponimod, sirolimus, sitafloxacin, sitagliptin, sitagliptinphosphate, sivelestat, sizofiran, smilagenin, S-modafinil, sobuzoxane, sodium aescinate, sodium ascorbate, sodium benzoate, sodium bicarbonate, sodium chromoglycate, sodium ferricgluconate complex, sodium glycididazole, sodium gualenate, sodium hyaluronate, sodium ibandronate, sodium nitrate, sodium nitrite, sodium oxybate, sodium phenylacetate, sodium phenylbutyrate, sodium polysulthionate, sodium prasteronesulfate, sodium pyruvate, sodium taurocholate, sodium thiosulfate, sodium zirconiumcyclosilicate, sofosbuvir, sofpironium bromide, solabegron, solifenacin, solithromycin, sonidegib, sonolisib, sophocarpine, sophoridine hydrochloride, sorafenib, sorbitol, sotagliflozin, sotirimod, sotrastaurin, sotylize, sovaprevir, sparfloxacin, sparsentan, spebrutinib, spirapril, spironolactone, squalamine, stannsoporfin, stavudine, S-tenatoprazole, stepronin, stiripentol, streptozocin, strontium malonate, strontium ranelate, succinic acid, sucralfate, sucroferric oxyhydroxide, sufentanil, suftalanzinc, sugammadex, sulbactam, sulbactam sodium, sulcardine sulfate, sulfamethoxypyrazine, sulfasalazine, sulfatinib, sulfonylurea, sulforaphane, sulfotanshinone sodium, sulindac, sulodexide, sulphamethoxazole, sulthiame, sumatriptan, sumatriptan succinate, sunitinib, sunstone, suplasyn, suplatast tosilate, suramin sodium, verapamil hydrochloride, rilpivirine, sutezolid, suvorexant, tacalcitol, tacrine, tacrolimus, tadalafil, tafamidis, tafenoquine, tafluprost, tafoxiparin sodium, taladegib, talaporfin, talazoparib, talipexole, taltirelin, tamibarotene, tamoxifen, tamsulosin, tamsulosin hydrochloride, tandospirone, tanespimycin, tapentadol, tarafenacin, tarenflurbil, tarloxotinib bromide, taselisib, tasimelteon, tasquinimod, tavaborole, tavilermide, tazarotene, tazemetostat, tazobactam, tazobactam sodium, tebipenem pivoxil, tecarfarin, tecovirimat, tectorigenin sodiumsulfonate, tedisamil, tedizolid phosphate, tefinostat, tegafur, tegaserod, teicoplanin, telaprevir, telapristone acetate, telatinib, telbivudine, telithromycin, telmisartan, telotristatetiprate, temanogrel, temocapril, temoporfin, temozolomide, temsirolimus, tenalisib, tenapanor, teneligliptin, tenofovir, tenofoviralafenamide, tenofovirdipivoxil fumarate, tenofovir disoproxil aspartate, tenofovir disoproxil fumarate, tenoxicam, tepotinib, teprenone, terameprocol, terazosin, terbinafine, terbinafine hydrochloride, terguride, teriflunomide, tesevatinib, tesofensine, testosterone, testosterone undecanoate, tetrabenazine, tetracaine, tetracaine hydrochloride, tetrahydrocannabidiol, tetrathiomolybdate, tetryzoline, tezacaftor, thalidomide, theliatinib, theophylline, therapeutic, thiazide, thienorphine hydrochloride, thiotepa, thrombin, thromboreductin, thyroxine, tiagabine, tianeptine, tibolone, ticagrelor, ticlopidine, tigecycline, tiludronatedi sodium, timolol, timolol maleate, tindamax, tinidazole, tinzaparin sodium, tioconazole, tiopronin, tiotropium bromide, tiotropium bromide monohydrate, tipelukast, tipepidine hibenzate, tipifarnib, tipiracil hydrochloride, tipranavir, tirapazamine, tirasemtiv, tirilazad, tirofiban, tirofiban hydrochloride, tivantinib, tivozanib, tizanidine, tobramycin, tocofersolan, tocoretinate, tofacitinib, tofogliflozin, tolcapone, tolimidone, tolperisone, tolterodine, tolterodine tartrate, tolvaptan, tonabersat, topiramate, topiroxostat, topotecan, topotecan hydrochloride, torasemide, toreforant, toremifene, tosedostat, tosufloxacin, totrombopag, tozadenant, trabectedin, trabodenoson, tradipitant, tramadol, tramadol hydrochloride, trametinib, trandolapril, tranexamic acid, tranilast, transcrocetinate-sodium, transepithelial riboflavin, trantinterol hydrochloride, travoprost, trazodone, trehalose, trelagliptin succinate, treosulfan, treprostinil, treprostinil diolamine, tretinoin, triamcinolone acetonide, triapine, triazolam, tribendimidine, trichlormethiazide, triciribine, triclabendazole, triclocarban, trientine hydrochloride, trifarotene, trifluridine, triflusal, triheptanoin, trilostane, trimebutine3-thiocarbamoyl-benzenesulfonate, trimebutine tosylate, trimegestone, trimethoprim, trimetrexate, trinitrate, tripotassium dicitratobismuthate, trofinetide, tropicamide, tropisetron, trospiumchloride, trovafloxacin, troxipide, tucatinib, tulobuterol, tylerdipinehydrochloride, ubenimex, ubidecarenone, ubrogepant, udenafil, ulinastatin, ulipristal, ulixertinib, ulobetasol, umeclidinium, umeclidinium bromide, upamostat, uprosertib, uracil, urapidil, uridinetriacetate, uroacitides, ursodeoxycholic acid, ursolicacid, vaborbactam, vadadustat, valaciclovir, valaciclovir hydrochloride, valbenazine, valdecoxib, valganciclovir, valomaciclovir stearate, valproic acid, valrubicin, valsartan, valsartan trisodium hemipentahydrate, vancomycin, vancomycin hydrochloride, vandetanib, vaniprevir, vanoxerine, vapendavir, vardenafil hydrochloride, varenicline, varithena, varlitinib, vatiquinone, vavelta, veliparib, velpatasvir, velusetrag, vemurafenib, venetoclax, venlafaxine, venlafaxine hydrochloride, vepoloxamer, verapamil, verapamil hydrochloride, verdinexor, veregen, vericiguat, verinurad, vernakalant, vernakalant hydrochloride, verosudil, verteporfin, verubecestat, verubulin, vesatolimod, vesnarinone, vibegron, vicagrel, vigabatrin, vilanterol, vilanterol trifenatate, vilaprisan, vilazodone, vildagliptin, vincristine sulfate, vinflunine, vinorelbine, vinpocetine, vintafolide, viralym-C, vismodegib, vistusertib, vitamin E nicotinicate, vizomitin, voglibose, volasertib, volixibat potassium ethanolate hydrate, vonoprazan fumarate, vorapaxar, voriconazole, vorinostat, vortioxetine, vortioxetine hydrobromide, vosaroxin, voxilaprevir, warfarin, xemilofiban, yimitasvir, yonkenafil, zabofloxacin, zafirlukast, zalcitabine, zaleplon, zaltoprofen, zamicastat, zanamivir, zemiStatin, Z-endoxifen hydrochloride, zibotentan, zidebactam, zidovudine, zileuton, zincacetate, zinostatin stimalamer, ziprasidone, zofenopril, zogenix, zoledronate D,L-lysinemonohydrate, zoledronate disodium, zoledronic acid, zoliflodacin, zolmitriptan, zolpidem, zolpidem tartrate, zonisamide, zopiclone, zotepine, zucapsaicin, zuclopenthixol, and zuretinol acetate.

In certain embodiments, traditional Chinese medicine is selected from the group consisting of Abelmoschi Corolla, Abri Herba, Abutili Semen, Acanthopanacis Cortex Acanthopanacis Senticosi Radix Et Rhizoma Seu Caulis, Acanthopanax Extract, Achilleae Herba, Achyranthis Bidentatae Radix, Aconiti Kusnezoffii Folium, Aconiti Kusnezoffii Radix Cocta, Aconiti Kusnezoffii Radix, Aconiti Lateralis Radix Praeparata, Aconiti Radix Cocta, Aconiti Radix, Acori Calami Rhizoma, Acori Tatarinowii Rhizoma, Adenophorae Radix, Aesculi Semen, Agkistrodon, Agrimoniae Herba, Ailanthi Cortex, Ajugae Herba, Akebiae Caulis, Akebiae Fructus, Albiziae Cortex, Albiziae Flos, Alismatis Rhizoma, Allii Macrostemonis Bulbus, Allii Sativi Bulbus, Allii Tuberosi Semen, Aloe, Alpiniae Katsumadai Semen, Alpiniae Officinarum Rhizoma, Alpiniae Oxyphyllae Fructus, Alumen, Amomi Fructus Rotundus, Amomi Fructus, Ampelopsis Radix, Andrographis Herba, Andrographolides, Anemarrhenae Rhizoma, Anemones Raddeanae Rhizoma, Angelicae Dahuricae Radix, Angelicae Pubescentis Radix, Angelicae Sinensis Radix, Anisi Stellati Fructus, Apocyni Veneti Folium, Aquilariae Lignum Resinatum, Arcae Concha, Arctii Fructus, Ardisiae Crenatae Radix, Ardisiae Japonicae Herba, Arecae Pericarpium, Arecae Semen Tostum, Arecae Semen, Arisaema Cum Bil, Arisaematis Rhizoma Preparatum, Arisaematis Rhizoma, Aristolochiae Fructus, Aristolochiae Herba, Armeniacae Semen Amarum, Arnebiae Radix, Artemisia Annuae Herba, Artemisiae Argyi Folium, Artemisiae Scopariae Herba, Asari Radix Et Rhizoma, Asiatic Moonseed Root Extract, Asini Corii Colla, Asparagi Radix, Aspongopus, Asteris Radix Et Rhizoma, Astragali Complanati Semen, Astragali Radix Praeparata Cum Melle, Astragali Radix, Atractylodis Macrocephalae Rhizoma, Atractylodis Rhizoma, Aucklandiae Radix, Aurantii Fructus Immaturus, Aurantii Fructus, Bambusae Caulis In Taenias, Bambusae Concretio Silicea, Baphicacanthis Cusiae Rhizoma Et Radix, Belamcandae Rhizoma, Belladonna Extract, Belladonna Liquid Extract, Belladonnae Herba, Benincasae Exocarpium, Benzoinum, Berberidis Radix, Bergeniae Rhizoma, Bergenin, Bistortae Rhizoma, Bletillae Rhizoma, Bolbostemmatis Rhizoma, Bombyx Batryticatus, Borneolum Syntheticum, Borneolum, Bovis Calculus Artifactus, Bovis Calculus Sativus, Bovis Calculus, Breviscapine, Broussonetiae Fructus, Bruceae Fructus, Bubali Cornu, Buddlejae Flos, Bufonis Venenum, Bungarus Parvus, Bupleuri Radix, Calamina, Callicarpae Caulis Et Folium, Callicarpae Formosanae Folium, Callicarpae Macrophyllae Folium, Calomelas, Campsis Flos, Canarii Fructus, Canavaliae Semen, Cannabis Fructus, Capsici Fructus, Carotae Fructus, Carpesii Fructus, Carthami Flos, Caryophylli Flos, Caryophylli Fructus, Cassiae Semen, Castor Oil, Catechu, Celosiae Cristatae Flos, Celosiae Semen, Centella Total Glucosides, Centellae Herba, Centipedae Herba, Cera Chinensis, Cera Flava, Cervi Cornu Degelatinatum, Cervi Cornu Pantotrichum, Cervi Cornu, Cervi Cornus Colla, Chaenomelis Fructus, Changii Radix, Chebulae Fructus Immaturus, Chebulae Fructus, Chelidonii Herba, Chinese Angelica Liquid Extract, Chloriti Lapis, Choerospondiatis Fructus, Chrysanthemi Flos, Chrysanthemi Indici Flos, Chuanxiong Rhizoma, Cibotii Rhizoma, Cicadae Periostracum, Cichorii Herba, Cichorii Radix, Cimicifugae Rhizoma, Cinnabaris, Cinnamomi Cortex, Cinnamomi Ramulus, Cinnamon Oil, Cirsii Herba, Cirsii Japonici Herba Carbonisata, Cirsii Japonici Herba, Cissampelotis Herba, Cistanches Herba, Citri Exocarpium Rubrum, Citri Fructus, Citri Grandis Exocarpium, Citri Reticulatae Pericarpium Viride, Citri Reticulatae Pericarpium, Citri Reticulatae Semen, Citri Sarcodactylis Fructus, Clematidis Armandii Caulis, Clematidis Radix Et Rhizoma, Clinopodii Herba, Cnidii Fructus, Codonopsis Radix, Coicis Semen, Commelinae Herba, Conyzae Herba, Coptidis Rhizoma, Cordyceps, Corni Fructus, Corydalis Bungeanae Herba, Corydalis Decumbentis Rhizoma, Corydalis Rhizoma, Crataegi Folium, Crataegi Fructus, Cremastrae Pseudobulbus, Pleiones Pseudobulbus, Crinis Carbonisatus, Croci Stigma, Crotonis Fructus, Crotonis Semen Pulveratum, Curculiginis Rhizoma, Curcumae Longae Rhizoma, Curcumae Radix, Curcumae Rhizoma, Cuscutae Semen, Cyathulae Radix, Cyclovirobuxine, Cynanchi Atrati Radix Et Rhizoma, Cynanchi Paniculati Radix Et Rhizoma, Cynanchi Stauntonii Rhizoma Et Radix, Cynomorii Herba, Cyperi Rhizoma, Dahurian Rhododendron Leaf Oil, Dalbergiae Odoriferae Lignum, Daturae Flos, Dendrobii Caulis, Dendrobii Officinalis Caulis, Descurainiae Semenlepidii Semen, Desmodii Styracifolii Herba, Dianthi Herba, Dichroae Radix, Dictamni Cortex, Dioscorea Panthaicae Rhizoma, Dioscoreae Hypoglaucae Rhizoma, Dioscoreae Nipponicae Rhizoma, Dioscoreae Rhizoma, Dioscoreae Spongiosae Rhizoma, Dipsaci Radix, Draconis Sanguis, Drynariae Rhizoma, Dryopteridis Crassirhizomatis Rhizoma Carbonisatum, Dryopteridis Crassirhizomatis Rhizoma, Echinopsis Radix, Ecliptae Herba, Entadae Semen, Entianae Rhodanthae Herba, Ephedrae Herba, Ephedrae Radix Et Rhizoma, Epimedii Folium, Epimedii Wushanensis Folium, Equiseti Hiemalis Herba, Erigerontis Herba, Eriobotryae Folium, Eriocauli Flos, Erodii Herba Geranii Herba, Erycibes Caulis, Eucalyptus Oil, Eucommiae Cortex, Eucommiae Folium, Euodiae Fructus, Eupatorii Herba, Eupatorii Lindleyani Herba, Euphorbiae Ebracteolatae Radix, Euphorbiae Hirtae Herba, Euphorbiae Humifusae Herba, Euphorbiae Pekinensis Radix, Euphorbiae Semen Pulveratum, Euphorbiae Semen, Eupolyphaga Steleophaga, Euryales Semen, Fagopyri Dibotryis Rhizoma, Farfarae Flos, Ferulae Resina, Fibraureae Caulis, Fibriuretinin, Fluoritum, Foeniculi Fructus, Forsythiae Fructus, Fraxini Cortex, Fritillariae Cirrhosae Bulbus, Fritillariae Hupehensis Bulbus, Fritillariae Pallidiflorae Bulbus, Fritillariae Thunbergii Bulbus, Fritillariae Ussuriensis Bulbus, Galangae Fructus, Galla Chinensis, Galli Gigerii Endothelium Corneum, Ganoderma, Capillary Wormwood Extract, GardeniaeFructus Praeparatus, Gardeniae Fructus, Gastrodiae Rhizoma, Gecko, Gei Herba, Gendarussae Herba, Genkwa Flos, Gentianae Macrophyllae Radix, Gentianae Radix Et Rhizoma, Ginger Liquid Extract, Ginkgo Folium, Ginkgo Leaves Extract, Ginkgo Semen, Ginseng Folium, Ginseng Radix Et Rhizoma Rubra, Ginseng Radix Et Rhizoma, Glabrous Sarcandra Extract, Glechomae Herba, Gleditsiae Fructus Abnormalis, Gleditsiae Sinensis Fructus, Gleditsiae Spina, Glehniae Radix, Glycyrrhizae Radix Et Rhizoma Praeparata Cum Melle, Glycyrrhizae Radix Et Rhizoma, Gossampini Flos, Granati Pericarpium, Gypsum Fibrosum, Gypsum Ustum, Haematitum, Haliotidis Concha, Halitum, Halloysitum Rubrum, Hawthorn Leave Extract, Hedysari Radix Praeparata Cum Melle, Hedysari Radix, Hibisci Mutabilis Folium, Hippocampus, Hippophae Fructus, Hirudo, Homalomenae Rhizoma, Hordei Fructus Germinatus, Houttuyniae Herba, Hydrargyri Oxydum Rubrum, Hyoscyami Semen, Hyperici Perforati Herba, Ilicis Chinensis Folium, Ilicis Cornutae Folium, Ilicis Rotundae Cortex, Ulicii Cortex, Impatientis Semen, Imperatae Rhizoma, Indigo Naturalis, Inulae Flos, Inulae Herba, Inulae Radix, Iridis Tectori Rhizoma, Isatidis Folium, Isatidis Radix, Juglandis Semen, Jujubae Fructus, Junci Medulla, Kadsurae Caulis, Kaempferiae Rhizoma, Kaki Calyx, Kansui Radix, Knoxiae Radix, Kochiae Fructus, Lablab Semen Album, Laggerae Herba, Lagotidis Herba, Laminariae Thallus Eckloniae Thallus, Lamiophlomis Herba, Lasiosphaera Calvatia, Leonuri Fructus, Leonuri Herba, Leonurus Liquid Extract, Licorice Extract, Licorice Liquid Extract, Ligustici Rhizoma Et Radix, Ligustri Lucidi Fructus, Lilii Bulbus, Limonitum, Linderae Radix, Lini Semen, Liquidambaris Fructus, Liquidambaris Resina, Liriopes Radix, Litchi Semen, Litseae Fructus, Lobeliae Chinensis Herba, Longan Arillus, Lonicerae Flos, Lonicerae Japonicae Caulis, Lonicerae Japonicae Flos, Lophatheri Herba, Luffae Fructus Retinervus, Lycii Cortex, Lycii Fructus, Lycopi Herba, Lycopodii Herba, Lygodii Spora, Lysimachiae Herba, Lysionoti Herba, /-Borneolum, /-Menthol, Magnetitum, Magnoliae Flos, Magnoliae Officinalis Cortex, Magnoliae Officinalis Flos, Mahoniae Caulis, Malvae Fructus, Manis Squama, Mantidis OOTheca, Margarita, Margaritifera Concha, Marsdeniae Tenacissimae Caulis, Mel, Melanteritum, Meliae Cortex, Melo Semen, Menispermi Rhizoma, Menthae Haplocalycis Herba, Meretricis Concha, Cyclinae Concha, Micae Lapis Aureus, Microctis Folium, Mirabilitum Praeparatum, Momordicae Semen, Mori Cortex, Mori Folium, Mori Fructus, Mori Ramulus, Morindae Officinalis Radix, Moschus, Moslae Herba, Moutan Cortex, Mume Flos, Mume Fructus, Murrayae Folium Et Cacumen, Mylabris, Myristicae Semen, Myrrha, Nardostachyos Radix Et Rhizoma, Natrii Sulfas Exsiccatus, Natrii Sulfas, Nelumbinis Folium, Nelumbinis Plumula, Nelumbinis Receptaculum, Nelumbinis Rhizomatis Nodus, Nelumbinis Semen, Nelumbinis Stamen, Nigellae Semen, Notoginseng Radix Et Rhizoma, Notoginseng Total Saponins, Notoginseng Triol Saponins, Notopterygii Rhizoma Et Radix, Ocimum Gratissimum Oil, Olibanum, Omphalia, Ophicalcitum, Ophiopogonis Radix, Orostachyis Fimbriatae Herba, Oroxyli Semen, Oryzae Fructus Germinatus, Osmundae Rhizoma, Ostreae Concha, Paeoniae Radix Alba, Paeoniae Radix Rubra, Panacis Japonici Rhizoma, Panacis Majoris Rhizoma, Panacis Quinquefolii Radix, Papaveris Pericarpium SI, Paridis Rhizoma, Patchouli Oil, Pegaeophyti Radix Et Rhizoma, Peppermint Oil, Perillae Caulis, Perillae Folium, Perillae Fructus, Periplocae Cortex, Persicae Ramulus, Persicae Semen, Peucedani Decursivi Radix, Peucedani Radix, Pharbitidis Semen, Phellodendri Amurensis Cortex, Phellodendri Chinensis Cortex, Pheretima, Phragmitis Rhizoma, Phyllanthi Fructus, Physalis Calyx Seu Fructus, Physochlainae Radix, Phytolaccae Radix, Picrasmae Ramulus Et Folium, Picriae Herba, Picrorhizae Rhizoma, Pinelliae Rhizoma Praeparatum Cum Alumine, Pinelliae Rhizoma Praeparatum Cum Zingibere Et Alumine, Pinelliae Rhizoma Praeparatum, Pinelliae Rhizoma, Pini Lignum Nodi, Pini Pollen, Piperis Fructus, Piperis Kadsurae Caulis, Piperis Longi Fructus, Plantaginis Herba, Plantaginis Semen, Platycladi Cacumen, Platycladi Semen, Platycodonis Radix, Pogostemonis Herba, Polygala Liquid Extract, Polygalae Japonicae Herba, Polygalae Radix, Polygonati Odorati Rhizoma, Polygonati Rhizoma, Polygoni Avicularis Herba, Polygoni Cuspidati Rhizoma Et Radix, Polygoni Multiflori Caulis, Polygoni Multiflori Radix Praeparata, Polygoni Multiflori Radix, Polygoni Orientalis Fructus, Polygoni Perfoliati Herba, Polygoni Tinctorii Folium, Polyporus, Poria, Poriae Cutis, Portulacae Herba, Potentillae Chinensis Herba, Potentillae Discoloris Herba, Powerdered Buffalo Horn Extract, Prinsepiae Nux, Propolis, Prunellae Spica, Pruni Semen, Psammosilenes Radix, Pseudolaricis Cortex, Pseudostellariae Radix, Psoraleae Fructus, Pterocephali Herba, Puerariae Lobatae Radix, Puerariae Thomsonii Radix, Pulsatillae Radix, Pyritum, Pyrolae Herba, Pyrrosiae Folium, Quisqualis Fructus, Rabdosiae Rubescentis Herba, Ranae Oviductus, Ranunculi Ternati Radix, Raphani Semen, Realgar, Rehmanniae Radix Praeparata, Rehmanniae Radix, Rhapontici Radix, Rhei Radix Et Rhizoma, Rhodiolae Crenulatae Radix Et Rhizoma, Rhododendri Daurici Folium, Rhododendri Mollis Flos, Rhubarb Extract, Rhubarb Liquid Extract, Ricini Semen, Rosae Chinensis Flos, Rosae Laevigatae Fructus, Rosae Rugosae Flos, Rubi Fructus, Rubiae Radix Et Rhizoma, Saigae Tataricae Cornu, Salvia Total Phenolic Acids, Salviae Miltiorrhizae Radix Et Rhizoma, Sanguisorbae Radix, Santali Albi Lignum, Saposhnikoviae Radix, Sappan Lignum, Sarcandrae Herba, Sargassum, Sargentodoxae Caulis, Sauropi Folium, Saururi Herba, Saussureae Involucratae Herba, Schisandrae Chinensis Fructus, Schisandrae Sphenantherae Fructus, Schizonepetae Herba Carbonisata, Schizonepetae Herba, Schizonepetae Spica Carbonisata, Schizonepetae Spica, Scolopendra, Scorpio, Scrophulariae Radix, Scutellaria Extract, Scutellariae Barbatae Herba, Scutellariae Radix, Sedi Herba, Selaginellae Herba, Semiaquilegiae Radix, Senecionis Scandentis Hebra, Sennae Folium, Sepiae Endoconcha, Serpentis Periostracum, Sesame Oil, Sesami Semen Nigrum, Setariae Fructus Germinatus, Siegesbeckiae Herba, Silybi Fructus, Sinapis Semen, Sinomenii Caulis, Sinopodophylli Fructus, Siphonostegiae Herba, Siraitiae Fructus, Smilacis Chinae Rhizoma, Smilacis Glabrae Rhizoma, Sojae Semen Germinatum, Sojae Semen Nigrum, Sojae Semen Praeparatum, Solidaginis Herba, Sophorae Flavescentis Radix, Sophorae Flos, Sophorae Fructus, Sophorae Tonkinensis Radix Et Rhizoma, Sparganii Rhizoma, Spatholobi Caulis, Spiceleaf Kernel Oil, Spirodelae Herba, Stachyuri Medulla Helwingiae Medulla, Stalactitum, Star Anise Oil, Stauntoniae Caulis Et Folium, Stellariae Radix, Stemonae Radix, Stephaniae Tetrandrae Radix, Sterculiae Lychnophorae Semen, Strychni Semen Pulveratum, Strychni Semen, Styrax, Suis Fellis Pulvis, Sulfur, Swertiae Herba, Swertiae Mileensis Herba, Syngnathus, Syringae Cortex, Talci Pulvis, Talcum, Tamaricis Cacumen, Tanshinones, Taraxaci Herba, Taxilli Herba, Tea-Seed Oil, Terminaliae Belliricae Fructus, Testudinis Carapacis Et Plastri Colla, Testudinis Carapax Et Plastrum, Tetrapanacis Medulla, Thlaspi Herba, Thunberg Fritillary Liquid Extract, Tinosporae Radix, Toatal Ginsenoside Of Ginseng Stems And Leaves, Toosendan Fructus, Torreyae Semen, Total Ginsenoside Ginseng Root, Toxicodendri Resina, Trachelospermi Caulis Et Folium, Trachycarpi Petiolus, Tribuli Fructus, Trichosanthis Fructus, Trichosanthis Pericarpium, Trichosanthis Radix, Trichosanthis Semen Tostum, Trichosanthis Semen, Trigonellae Semen, Trionycis Carapax, Tsaoko Fructus, Turpentine Oil, Turpiniae Folium, Typhae Pollen, Typhonii Rhizoma, Uncariae Ramulus Cum Uncis, Vaccariae Semen, Valerianae Jatamansi Rhizoma Et Radix, Verbenae Herba, Vespae Nidus, Vignae Semen, Violae Herba, Visci Herba, Vitex Oil, Viticis Fructus, Viticis Negundo Folium, Vladimiriae Radix, Weeping Forsythia Extract, Wenyujin Rhizoma Concisum, Xanthii Fructus, Zanthoxyli Pericarpium, Zanthoxyli Radix, Zaocys, Zedoary Turmeric Oil, Zingiberis Rhizoma Praeparatum, Zingiberis Rhizoma Recens, Zingiberis Rhizoma, Ziziphi Spinosae Semen.

In certain embodiments, the drug content further comprises a medium. The medium can be associated with the API, i.e., the medium is in physical contact with the API. In certain embodiments, the API is embedded in the medium. In certain embodiments, the API is dispersed within the medium. In certain embodiments, the medium is made of a thermoplastic material as disclosed herein.

In certain embodiments, the medium comprises a water-soluble excipient selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructooligosaccharides and a combination thereof. In certain embodiments, the substrate further comprises a plasticizer.

The drug content can be of any suitable shape and size to be loaded into the compartment.

In certain embodiments, the drug content is operably linked to the compartment via covalent bond, non-covalent interactions or through a linker. Thus, the drug content and the substrate can be made separately and associate together through a covalent bond or non-covalent interactions. In certain embodiments, dosage form is made by producing the drug content and the substrate in a single process using 3D printing methods.

In certain embodiments, the drug content is formed in the shape of a compressed tablet, an oval tablet, a pill, or a capsule. In certain embodiments, the shape of the drug content matches the shape of the compartment. For example, when the compartment is a pie-shape, the drug content is also of a pie-shape, e.g., to fill the compartment.

Figure 6:
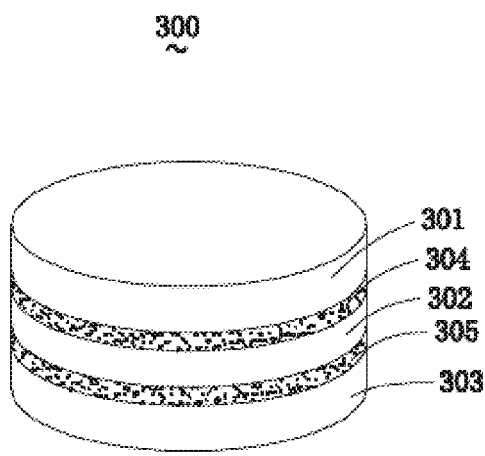
FIG. 6 shows an exemplary dosage form having a substrate that forms layers with drug content in the form of nanoparticles dispersed between the layers.

In certain embodiments, the drug content is in the form of nanoparticles as illustrated in FIG. 6. The drug content can be mixed with solution in which the API is either dissolved or suspended. The solution is then atomized/sprayed atop a printing layer during the course of the three-dimensional printing of the dosage form. Once the solution containing the drug content dries, the drug content is dispersed in the dosage form. Nanoparticles have large surface area and will have high dissolution rate.

The size of the nanoparticles ranges from 1 nm to 900 nm in size (preferable 100-800 nm, 100-700 nm, 100-600 nm, 100-500 nm, 100-400 nm, 100-300 nm, 100-200 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 100 nm, 200 nm, 300 nm, 400 nm, 500 nm, 600 nm, 700 nm, 800 nm, 900 nm in size). The size of nanoparticles can be controlled by selecting appropriate synthesis methods and/or systems. To obtain nanoparticles within a desired size range, the synthesis conditions may be properly controlled or varied to provide for, e.g., a desired solution concentration or a desired cavity range (a detailed review can be found at, e.g., Vincenzo Liveri, Controlled synthesis of nanoparticles in microheterogeneous systems, Published by Springer, 2006).

Figure 7:
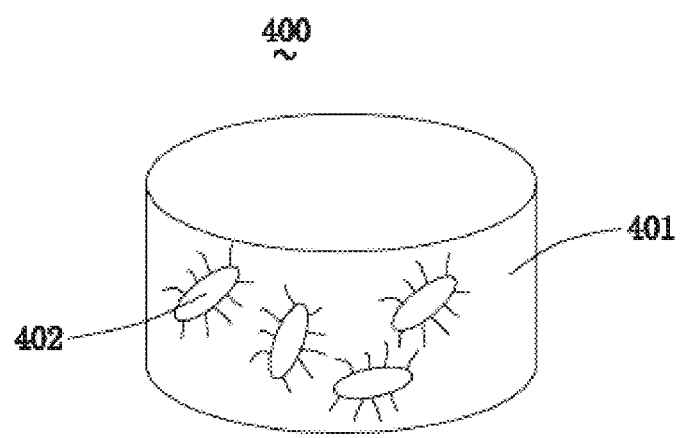
FIG. 7 shows an exemplary dosage form having a substrate that forms a compartment with a microneedle-shaped drug content loaded into the compartment.

In certain embodiments, the drug content is in the form of microneedles as illustrated in FIG. 7. The microneedle would be printed in conjunction with the dosage form or inserted into the dosage form during the three-dimensional printing of the dosage form. The microneedles can be composed of a saccharide, a PLGA polymer or an API or a combination thereof. The microneedle can assist in the penetration of an API into the circulatory system of a patient when administered either parenteral or enteric.

Figure 8A:
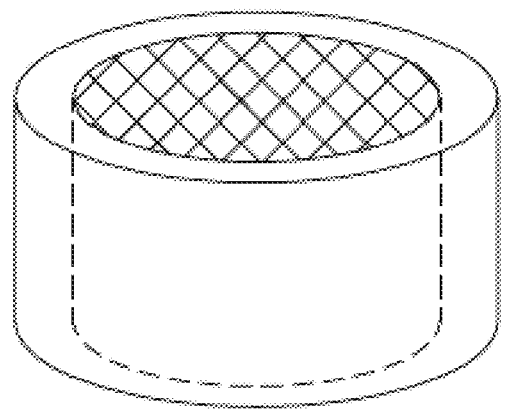
FIG. 8A shows an exemplary dosage form having a substrate forming a compartment loaded with a drug content. The drug content forms a network. The substrate is made of a material that dissolves between 1-5 minutes, and the drug content dissolves in seconds.
Figure 8B:
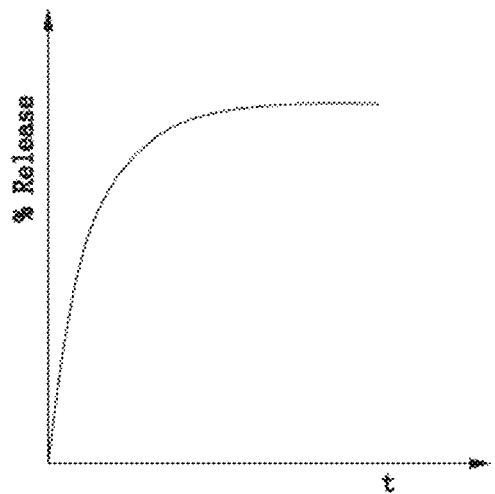
FIG. 8B shows the quick release of the API from the dosage form illustrated in FIG. 8A.

In certain embodiments, the drug content forms a network. As shown in FIG. 8A, a dosage form has a substrate forming a compartment loaded with a drug content. The drug content has a substrate forming a network. The frame structure of tablet is made of a material that dissolves between 1-10 minutes, and the substrate dissolves in 2-60 seconds, preferably in 2, 5, 10, 15, 20, 25, 30, 35, 40, 45, 50, 55, 60 seconds. As shown in FIG. 8B, the API can be released in seconds after the dosage form is administered. In certain embodiments, the substrate also forms a network, which can further accelerate the release of the API.

The drug content can be made using an additive method such as fused deposition modeling (FDM). In certain embodiments, the drug content can be made by using a three-dimensional printer (3D printer) configured to extruding a mixture of API and the excipient. The API can be melted and mixed homogenously with the melted substrate before being extruded. Alternatively, the API in a solid form (e.g., powder) can be mixed with and dispersed in the melted substrate before being extruded. In general, the extrusion process can be conducted at temperatures 10° to 40° C. above the glass transition (Tg) of the substrate and a temperature close to the melting point of the API. Once at a suitable temperature for use in the three-dimensional printer, the substrate can be deposited to the three-dimensional printing surface. The shape and size of the drug content can be controlled by programing the three-dimensional printing process. In certain embodiments, the drug content is fabricated in the same process of the substrate. In certain embodiments, the drug content is fabricated before the making of the substrate and loaded into the compartment during or after the substrate is fabricated.

In certain embodiments, when the drug content is loaded into the compartment, it is associated with the substrate, e.g., embedded or fixed in the substrate. In certain embodiments, the drug content is detachable from the substrate when loaded into the compartment.

D. Controlled Release

The dosage form disclosed herein can offer various release profiles after oral administration. In certain embodiments, the dosage form provides a constant release profile, pulsatile or delayed delivery, or non-linear drug release. In certain embodiments, the dosage form provides a zero-order release kinetics.

A proper release profile may offer benefits to certain drug therapy regimes. For example, a pulsatile release profile offers controlled absorption with resultant reduction in peak through ratios, targeted release of the drug to specific areas within the gastro intestinal tract, and absorption independent of the feeding state, thus may be used to prevent tolerance, reduce the side-effects and improve patient compliance, which is desirable to treat diseases like ADHD. For another example, a release profile with a loading dose followed by a maintenance dose may be good for treating chronic conditions such as hypertension and diabetes.

Some of the mechanisms to control the release profile using the dosage from disclosed herein have been discussed above. For example, by manipulating the exposed surface area of the substrate that erodes constantly over time, the drug content embedded in the substrate is able to deliver a constant amount of drug over time. In addition, the release profile can be controlled by the size of compartment opening and/or by the geometric shape of the compartment.

Figure 9:
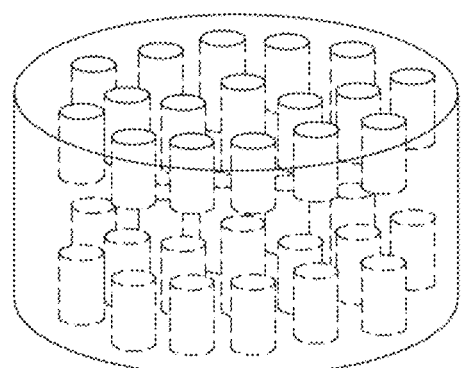
FIG. 9 shows an exemplary dosage form having a substrate forming a plurality of column-shaped compartments. Each compartment is loaded with one drug content. The release of the drug content can be controlled by the number and size of the compartments.

In certain embodiments, the release profile can be controlled by the design of a compartment having an aperture that is sealed or blocked by a plug. The plug is made of a water-soluble, porous, or erodible material or pH sensitive materials or hydrophobic material that will undergo attrition when the dosage form passing the GI tract. When the dosage form is administered to a subject, the plug is dissolved, permeated or eroded, thus releasing the drug content from the compartment. The release profile of the drug content can be controlled by choosing a plug of proper erosion/dissolution rate or permeation rate. Alternatively, the release profile of the drug content can be controlled by using the shape and/or the size of the plug (e.g., a rod shape of proper length). The release profile can also be controlled by the number of the compartment. FIG. 9 shows an exemplary dosage form having a substrate forming a plurality of column-shaped compartments residing on both sides of the dosage form. Each compartment is loaded with a drug content. Each compartment has an aperture that is blocked by a rod-shaped plug. The plugs have different dissolution rate. Depending on the size, shape and dissolution rate of the plug, the APIs can be released in a sustained, continuous, simultaneous, consecutive or pulsatile manner.

Figure 10A:
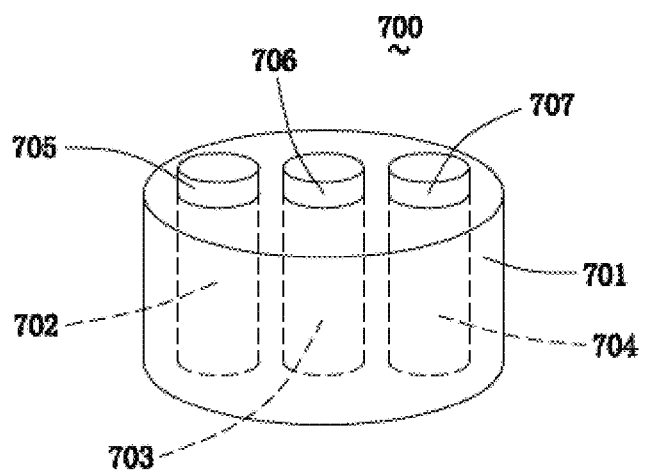
FIG. 10A shows an exemplary dosage form having a substrate forming three column-shaped compartments. Each compartment is loaded with one drug content. Each drug content has a plug that blocks the aperture of each compartment.

FIG. 10A shows an exemplary dosage form providing a consecutive release profile. Referring FIG. 10A, the dosage form 700 has a substrate 701 forming three column-shaped compartments 702~704. Each compartment is loaded with a drug content of the same API. Each compartment has an aperture that is blocked by a rod-shaped plug 705~707. The plugs are made of the same material but have different length. Consequently, it takes different amount of time to dissolve the plugs and to open the compartments to release the drug content. As illustrated in FIG. 10C, the shortest plug dissolves first, releasing the API from the first compartment. When the API in the first compartment is completely released, the plug of the median length dissolves, releasing the API from the second compartment. When the API in the second compartment is completely released, the third plug dissolves to release the API from the third compartment. As a result, the plasma drug level reaches the first peak when the drug content in the first compartment is released. When the API released from the first compartment starts to be eliminated, the plasma drug level starts to decrease (see FIG. 10D). Before the plasma drug level falls below the critical level (the horizontal line, below which the drug would be ineffective), the API from the second compartment is released, and the plasma drug level increases again. When the API released from the second compartment reaches the second peak and starts to be eliminated, the plug of the third compartment dissolves to open the compartment. As a result, the plasma API level is maintained above the critical level for a long time, which benefits certain diseases.

Figure 10B:
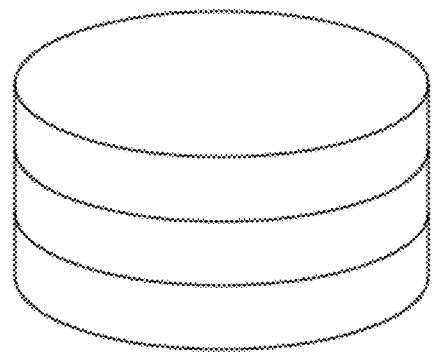
FIG. 10B shows an exemplary dosage form having a multiple-layered substrate with drug content embedded into each layer.
Figure 10C:
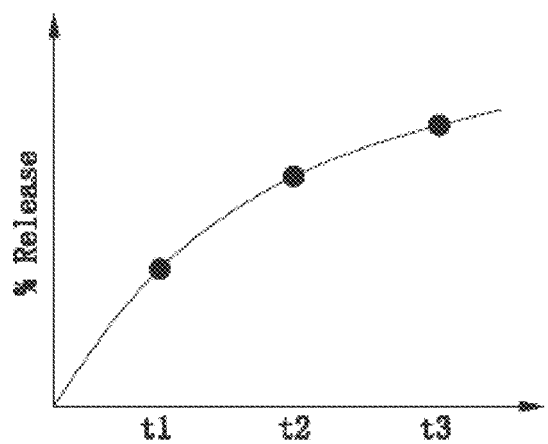
FIG. 10C shows the consequential release of the drug content from the dosage form illustrated in FIG. 10A or 10B.
Figure 10D:
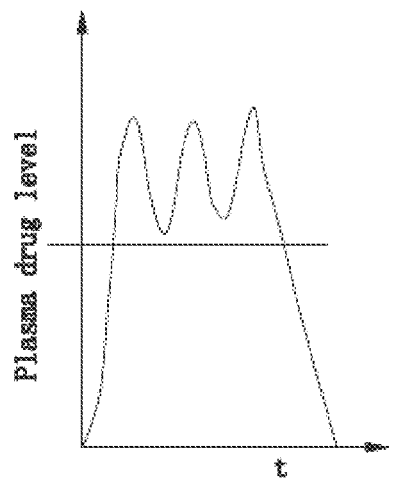
FIG. 10D shows the plasma drug level of the controlled release dosage form illustrated in FIG. 10A or 10B when administered to a subject.

The consecutive release manner can also be achieved through another exemplary dosage form having several drug contents packed in the form of layers as illustrated in FIG. 10B. The API can be released in a sustained manner by having each layer dissolving in synchrony to provide a continuous, sustained release of API as depicted in FIG. 10C. In certain embodiments, the outer layers of the dosage form dissolve immediately and release the embedded drug content when the dosage form is administered. But the layers sandwiched in the middle do not dissolve or dissolve much slower because the outer layers block their interface with the environment. The dissolution of the outer layers exposes the layers sandwiched in the middle and expedites their dissolution, thus providing a consecutive release profile as illustrated in FIG. 10C.

In certain embodiments, the dosage form comprises a gas-generating component loaded into the first compartment. In certain embodiments, the gas-generating component is selected from the group consisting of organic acid and carbonates, sulphites, bicarbonates, sodium carbonate, sodium bicarbonate, sodium metabisulphite, calcium carbonate, and combinations thereof, which on contact with gastric fluid releases carbon dioxide or sulphur dioxide gas. When the substrate is dissolved, permeated or eroded in stomach, the gas generating component is exposed to the acid environment or water penetrate into compartment to induce the reaction between acid and sodium bicarbonate and generates gas to release the drug content in an effervescent manner.

The dosage form disclosed herein may comprise one or more drug content at least partially in delayed-release form, wherein the delayed release may be achieved with the assistance of conventional materials and methods known to the person skilled in the art, for example by embedding the API in a delayed-release substrate/substrate or by the application of one or more delayed-release coatings. Through delayed release, API release may be so controlled that twice or once daily administration of the dosage form is sufficient, which is advantageous in particular in the case of a need for a sustained level active compound, e.g., for combatting pain.

In certain embodiments, the dosage form intends to release the active ingredients in oral cavity instantly. One example is to be given to oral cavity or take sublingual region.

In certain embodiments, the drug form can further comprise conventional auxiliary substances known to the person skilled in the art, preferably selected from the group consisting of glyceryl monostearate, semi-synthetic triglyceride derivatives, semi-synthetic glycerides, hydrogenated castor oil, glyceryl palmitostearate, glyceryl behenate, polyvinylpyrrolidone, gelatin, magnesium stearate, stearic acid, sodium stearate, talcum, sodium benzoate, boric acid and colloidal silica, fatty acids, substituted triglycerides, glycerides, polyoxyalkylene glycols and the derivatives thereof.

Manufacture of the Dosage Form

The controlled release dosage forms disclosed herein can be manufactured using any appropriate process. In certain embodiments, the dosage forms are produced using three-dimensional printing (3D printing).

As used herein, 3D printing refers to a process that produce 3D objects layer-by-layer from digital designs. The basic process of 3D printing has been described in U.S. Pat. Nos. 5,204,055; 5,260,009; 5,340,656; 5,387,380; 5,503,785; and 5,633,021. Additional U.S. patents and applications related to 3D printing include: U.S. Pat. Nos. 5,490,962; 5,518,690; 5,869,170; 6,530,958; 6,280,771; 6,514,518; 6,471,992; 8,828,411; U.S. PG Pub. Nos: 2002/0015728; 002/0106412; 2003/0143268; 2003/0198677; 2004/0005360. Reference can be made to the patents and applications listed above for a detailed description of 3D printing.

Different 3D printing methods have been developed for dosage form manufacturing in terms of raw materials, equipment and solidification. These 3D printing methods include binder deposition (see L Gibson et al. (2015) Additive Manufacturing Technologies: 3D Printing, Rapid Prototyping, and Direct Digital Manufacturing. 2 ed. Springer, New York; W. E. Katstra et al. (2000) Oral dosage forms fabricated by three dimensional printing, J. Control Release 66:1-9; W. E. Katstra et al. (2001) Fabrication of complex oral delivery forms by three dimensional printing, Dissertation in Materials Science and Engineering, Massachusetts Institute of Technology; H. Lipson et al. (2013) Fabricated: The New World of 3D printing, John Wiley & Sons, Inc.; G. Jonathan, A. Karim (2016) 3D printing in pharmaceutics: a new tool for designing customized drug delivery systems, Int. J. Pharm. 499:376-394), material jetting (see G. Jonathan, A. Karim (2016) 3D printing in pharmaceutics: a new tool for designing customized drug delivery systems, Int. J. Pharm. 499:376-394), extrusion (see L Gibson et al. (2015) Additive Manufacturing Technologies: 3D Printing, Rapid Prototyping, and Direct Digital Manufacturing. 2 ed. Springer, New York) and photopolymerization (see F. P. Melchels et al. (2010) A review on stereolithography and its application in biomedical engineering. Biomaterials 31:6121-30).

In certain embodiments, the dosage forms disclosed herein are manufactured using extrusion methods. In an extrusion process, material is extruded from robotically-actuated nozzles. Unlike binder deposition, which requires a powder bed, extrusion methods can print on any substrate. A variety of materials can be extruded for 3D printing, including thermoplastic materials disclosed herein, pastes and colloidal suspensions, silicones and other semisolids. One common type of extrusion printing is fused deposition modeling, which uses solid polymeric filaments for printing. In fused deposition modeling, a gear system drives the filament into a heated nozzle assembly for extrusion (see L Gibson et al. (2015) Additive Manufacturing Technologies: 3D Printing, Rapid Prototyping, and Direct Digital Manufacturing. 2 ed. Springer, New York).

The manufacturing instructions for a print job may be generated a variety of ways, including direct coding, derivation from a solid CAD model, or other means specific to the 3D printing machine's computer interface and application software. These instructions may include information on the number and spatial placement of droplets, and on general print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

Because of its ability of handling a range of pharmaceutical materials and control both composition and architecture locally, 3D printing is well suited to the fabrication of dosage forms with complex geometry and composition in accordance with the present invention.

Manufacturing the dosage forms using 3D printing methods also facilitate personalized medicine. Personalized medicine refers to stratification of patient populations based on biomarkers to aid therapeutic decisions and personalized dosage form design. Modifying digital designs is easier than modifying physical equipment. Also, automated, small-scale 3D printing may have negligible operating cost. Hence, 3D printing can make multiple small, individualized batches economically feasible and enable personalized dosage forms designed to improve adherence.

Personalized dosage form allows for tailoring the amount of drug delivered based on a patient's mass and metabolism. 3D printed dosage forms could ensure accurate dosing in growing children and permit personalized dosing of highly potent drugs. Personalized dosage forms can also combine all of patients' medications into a single daily dose, thus improve patients' adherence to medication.

Figure 11:
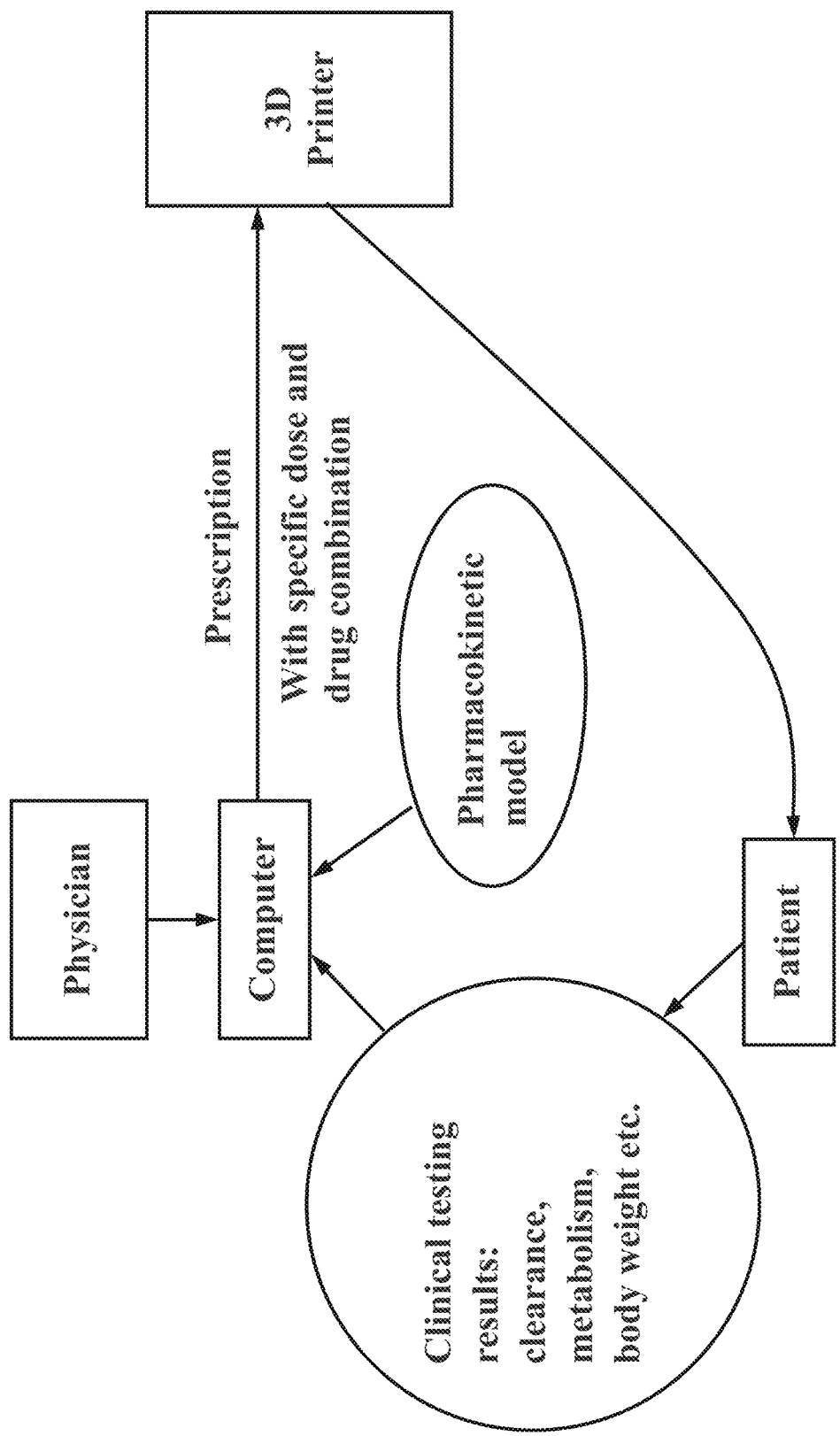
FIG. 11 is a schematic workflow for using of a three-dimensional printer for preparing patient specific dosage form.

FIG. 11 illustrates a process of using 3D printing to manufacture personalized dosage forms. For each patient, a variety of clinical testing results can be obtained, including body weight, age, metabolism indicator and genomic biomarkers, etc. The clinical testing results are input into computer software. The information is combined with the prescription of physician and pharmaco-kinetic model to design a dosage form of specific dose and drug combination. The instruction is then sent to a 3D printer to manufacture the dosage form designed, which is administered to the patient.

Controlled Release of Multiple Drugs

The dosage form and methods disclosed herein can be used to control release of two or more drugs in order to optimize the drug combinations in certain therapeutic regimes. For example, a tablet to treat hypercholesterolemia can be designed to offer immediate release of Atorvastatin calcium and extended release of nicotinic acid. In another example, a non-steroidal anti-inflammatory drug (NSAID) for pain relief may be designed to provide sustained release of NSAID and a rapid release of H2-receptor antagonist for preventing NSAID-induced mucosal damage.

In certain embodiments, the substrate forms multiple compartments, each loaded with a drug content. In certain embodiments, the multiple compartments are connected. In certain embodiments, the multiple compartments are disconnected. In certain embodiments, the drug contents loaded into different compartments are the same. In certain embodiments, the drug contents loaded into different compartments are different. The dosage form can be so designed to provide simultaneous or sequential release of multiple drug content to exert synergistic therapeutic effects.

Figure 12A:
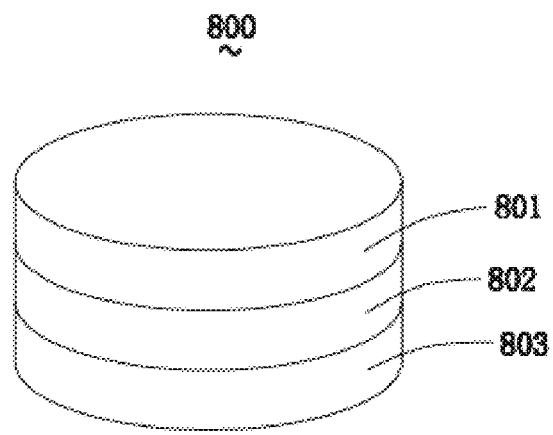
FIG. 12A shows an exemplary dosage form having a three-layered substrate with different drug content embedded into each layer.
Figure 12B:
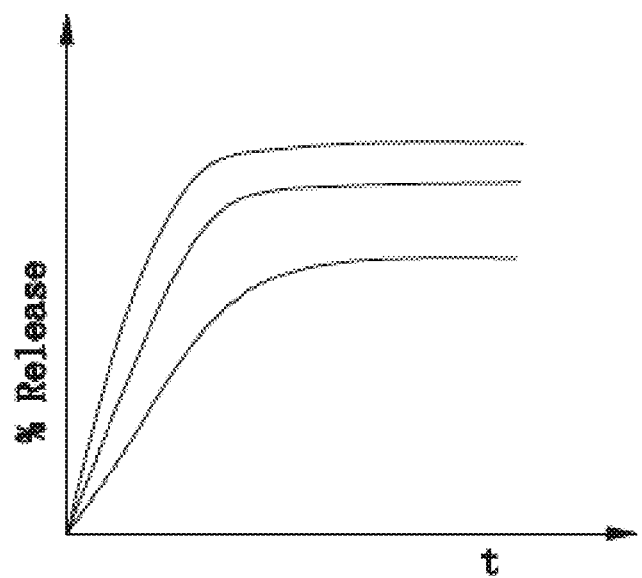
FIG. 12B illustrates the release of three APIs from the dosage form illustrated in FIG. 12A.

FIG. 12A shows an exemplary dosage form that can release APIs simultaneously. Referring to FIG. 12A, the dosage form 800 includes three stacked layers 801~803, each of which is embedded with a different drug content. As illustrated in FIG. 12B, when the dosage form 800 is administered, the drug contents are released simultaneously but at different rates as the layers dissolve.

Figure 13A:
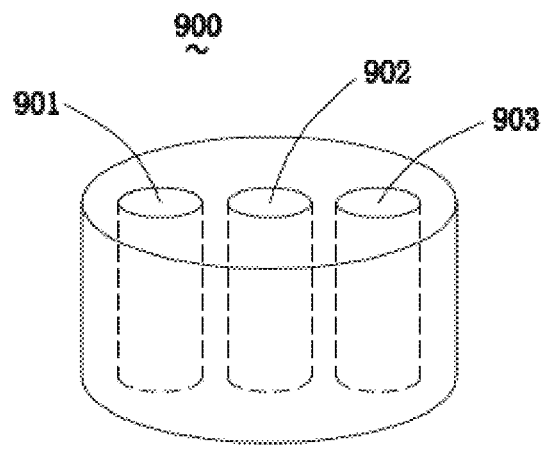
FIG. 13A shows an exemplary dosage form having a substrate forming three compartments, each of which loaded with one drug content. The release profile of the drug content can be controlled by the dissolution rate of the drug content.
Figure 13B:
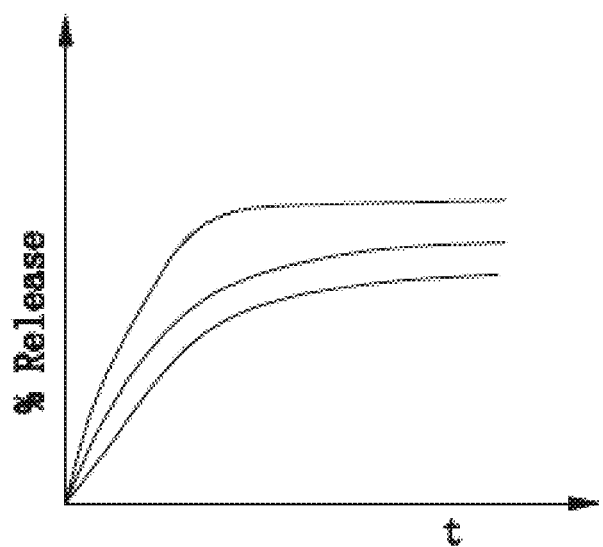
FIG. 13B illustrates the release profile of the APIs from the dosage form illustrated in FIG. 13A.

FIG. 13A depicts another exemplary dosage form of simultaneous release profile. Referring to FIG. 13A, the dosage form 900 includes three column shaped compartments 901~903, in which three drug contents are loaded. Each drug content contains an API embedded in a substrate of different dissolution rate. As illustrated in FIG. 13B, when the dosage form 900 is administered, the three APIs are released simultaneously but at different rates as the substrates of the drug contents dissolve. The release rate of the APIs can also be controlled by the shape of the compartments or the size of the opening of the compartments.

Figure 14A:
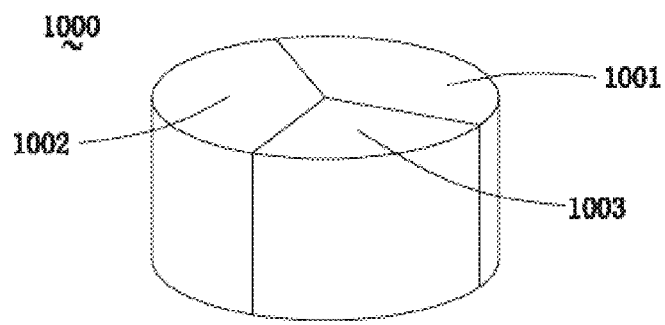
FIG. 14A shows an exemplary dosage form having a substrate having three pie-shaped segments, with drug content embedded into each segment.
Figure 14B:
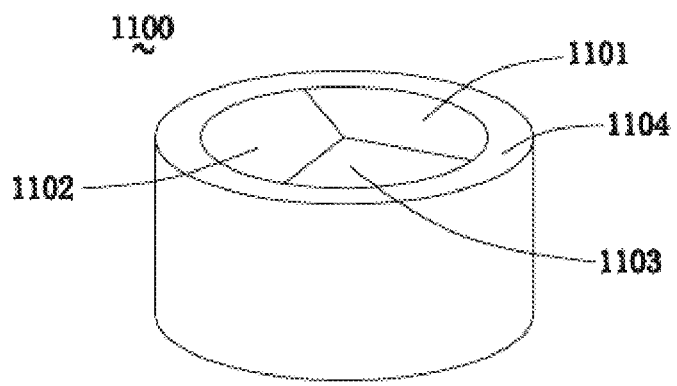
FIG. 14B shows an exemplary dosage form having a substrate having three pie-shaped segments wrapped with a shell structure.
Figure 14C:
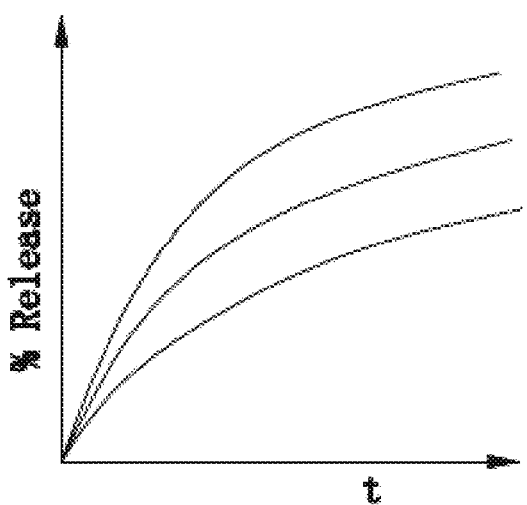
FIG. 14C shows the release profile of the APIs from the dosage forms illustrated in FIG. 8A and FIG. 8B.

FIGS. 14A and 14B depict additional exemplary dosage forms of simultaneous release profile of three APIs. Referring to FIG. 14A, the dosage form 1000 contains three pie-shaped segments 1001~1003 wherein drug contents are embedded. As illustrated in FIG. 14C, the drug contents release simultaneously as the segments dissolve, and the release rate of the drug contents can be controlled by the dissolution rate of the segments. Referring to FIG. 14B, the dosage form 1100 contains three pie-shaped segments 1101~1103, which are wrapped by a shell 1104 that dissolves slower than the segments. The release rates of the drug contents embedded in the segments are reduced as the shell 1104 blocks the interface of the segments 1101~1103 with the environment.

Figure 15A:
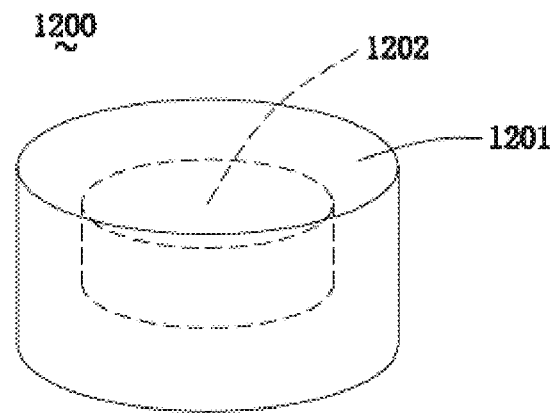
FIG. 15A shows an exemplary dosage form having a substrate forming a compartment filled with a drug content. A second API is embedded in the substrate and is released when the substrate dissolves.
Figure 15B:
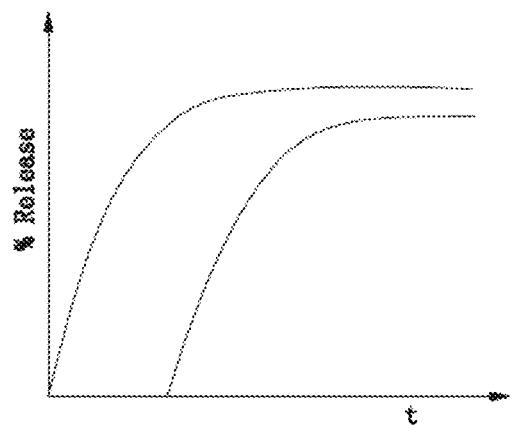
FIG. 15B shows the controlled release of the APIs from the dosage form illustrated in FIG. 15A.

FIG. 15A shows an exemplary dosage form of sequential release profile of two APIs. Referring to FIG. 15A, the dosage form 1200 includes a substrate 1201 forming a compartment that is filled by a drug content 1202. The substrate 1201 contains a first API, and the drug content 1202 contains a second API. As illustrated in FIG. 15B, the first API releases as the substrate dissolves when the dosage form is administered. The second API does not release until the substrate dissolves to expose the drug content, providing a sequential release profiles of the APIs.

Figure 16A:
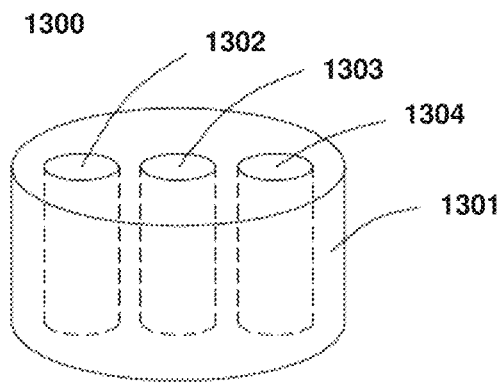
FIG. 16A shows an exemplary dosage form having a substrate forming three column-shaped compartments. Each compartment is loaded with one drug content. Each drug content has a plug that blocks the opening of each compartment. The release of the drug content in each compartment can be controlled by the permeability, degradability or erodibility of the plug.
Figure 16B:
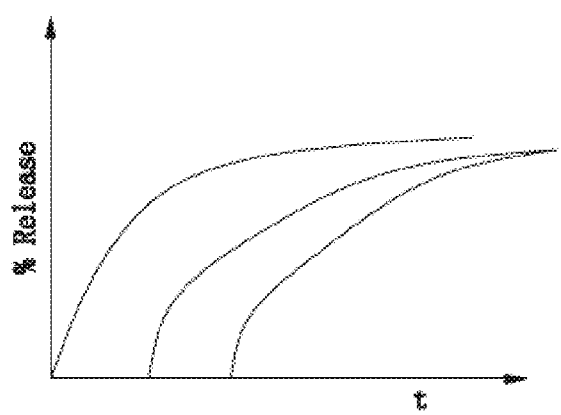
FIG. 16B shows the release profiles of the APIs from the dosage form illustrated in FIG. 16A.

FIG. 16A shows another exemplary dosage form of sequential release profiles. Referring to FIG. 16A, the dosage form 1300 has a substrate 1301 forming three column-shaped compartments 1302~1304 loaded with three drug contents. The compartments 1302~1304 have an aperture that are blocked by rod-shaped plugs that have different length and/or dissolution rate. As illustrated in FIG. 16B, the APIs are released in a sequential manner as the plugs dissolve sequentially to open the compartments.

Figure 17A:
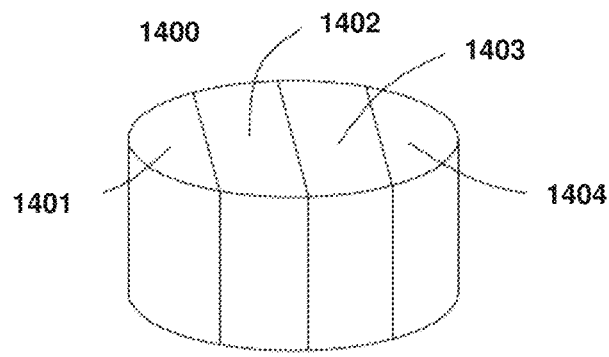
FIG. 17A shows an exemplary dosage form having a substrate forming four compartments. Each compartment is loaded with a drug content.
Figure 17B:
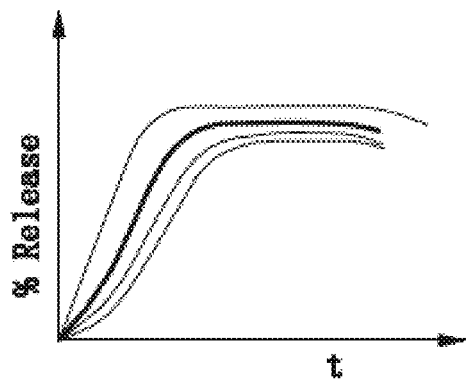
FIG. 17B shows the release of the APIs from a dosage form having a substrate consisted of four drug content embedded segments.
Figure 17C:
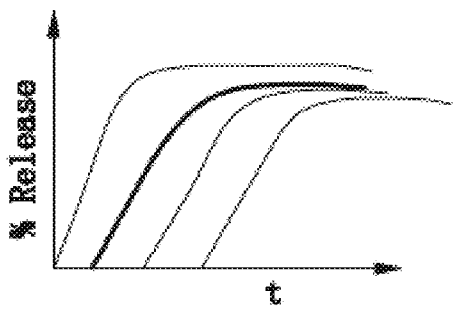
FIG. 17C shows the controlled release of the APIs from the dosage form illustrated in FIG. 17A.

FIG. 17A shows an exemplary dosage form having a simultaneous release profile or sequential release profile. Referring to FIG. 17A, the dosage form 1400 has a substrate containing four segments 1701~1704 having different dissolution rate. In certain embodiments, as illustrated in FIG. 17B, the drug contents are embedded in the segments 1701~1704 and are released simultaneously when the substrate dissolves. In certain embodiments, each segment contains a compartment where a drug content is loaded. As illustrated in FIG. 17C, the drug contents are released in a sequential manner when the substrate dissolves.

Example 1

This example illustrates a design of dosage form that has controlled release profile.

Figure 18A:
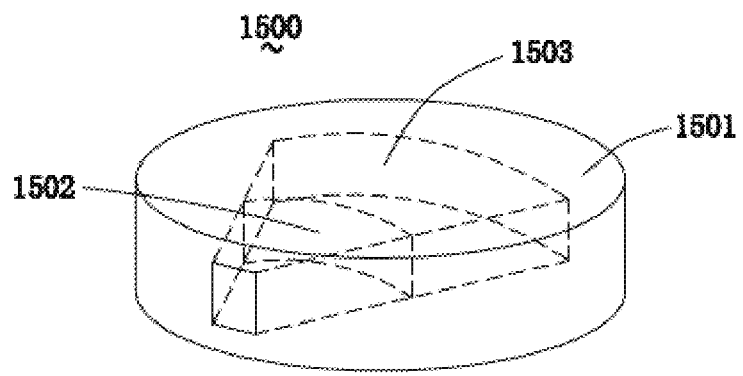
FIG. 18A is a schematic diagram of the drug form having a substrate forming a pie-shaped compartment.
Figure 18B:
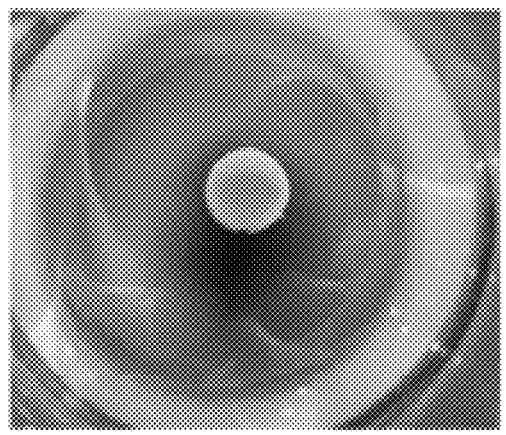
FIG. 18B is a photograph of a drug release processes of the drug form illustrated in FIG. 18A.

As shown in FIG. 18A, the dosage form comprised a flat tablet substrate forming a pie shaped compartment. The substrate was made of PEG8000. Benzoic acid was used as a module drug content.

Figure 18C:
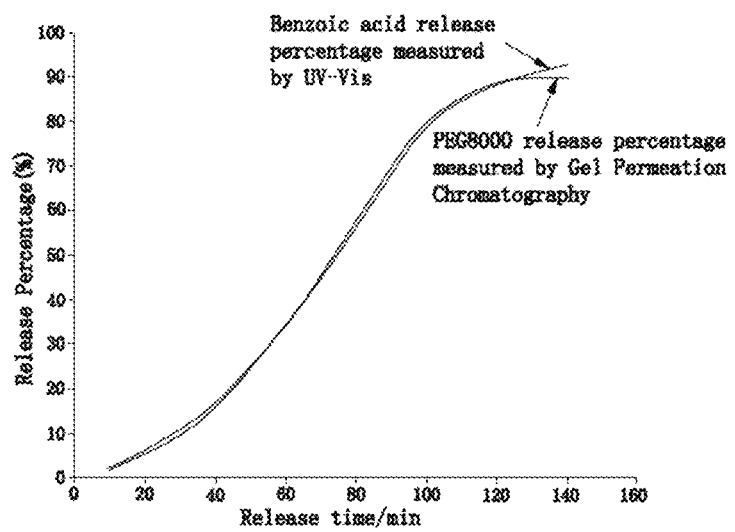
FIG. 18C shows release percentage curve of benzoic acid and PEG8000 from the dosage form of FIG. 18A.

The release profile of the benzoic acid from the dosage form was measured as the following method. $Na_2HPO_4$ solution of pH 8 was prepared as dissolvent of benzoic acid. Benzoic acid solution of 120 µg/mL was serially diluted to 30 µg/mL, 15 µg/m, 7.5 µg/m, 3.75 µg/mL, and 1.875 µg/mL solutions, whose absorbance at 226 nm was measured using a UV spectrophotometer. The numbers obtained were treated with linear regression to generate a standard curve of benzoic acid concentration with the formula y=0.0599x+0.0347. To measure the released amount of benzoic acid, the dosage form was dissolved in degassed pH 8 $Na_2HPO_4$ solution at 37° C.±0.5° C. and centrifuged at 100 rpm. 5 mL solution was collected from the solution at each time point to measure the concentration of benzoic acid with 5 mL dissolvent added back to the solution. The collected solution was filtered through 0.45 um membrane before transferred to an UV spectrophotometer for measuring the absorbance at 226 nm. The percentage of benzoic acid released was calculated using the following formula:

$$\text{Benzoic acid released}(\%) = \frac{C_n V_t + V_s \sum C_{n-1}}{Q_{benzoic\ acid}} \times 100$$

Wherein $C_n$ means concentrate measured, $V_t$ means total solution volume, $V_s$ means sample volume, $Q_{benzoic\ acid}$ means amount of benzoic acid in the dosage form The release of PEG8000 is measured using the following method. To prepare a standard curve of PEG8000, 0.1275 g PEG8000 standard sample was dissolved in water in a 25 mL volumetric flask. Transferring 1 mL, 2 mL 5 mL and 10 mL to 10 mL volumetric flask, respectively, and diluted in water to prepare the control solution. Injecting 50 ul control solutions to a liquid chromatography (three Waters Ultra-hydrogel™ 120/250/500 connected in series, flow speed at 0.5 ml/min, temperature at 40° C., measured by a differential refraction detector). The areas of the volume were measured and used as y-axis. The log numbers of the control solution concentration were used as x-axis. A standard curve of PEG8000 was generated with the formula of y=1.024x+ 8.918. The percentage of PEG800 released was calculated using the following formula:

$$PEG8000\ \text{released}(\%) = \frac{C_n V_t + V_s \sum C_{n-1}}{Q_{PEG8000}} \times 100$$

wherein $C_n$ means concentration measured, $V_t$ means volume of solution, $V_s$ means sample volume, $Q_{PEG8000}$ means amount of PEG8000 in the dosage form Results: as illustrated in FIG. 18C, the release profile of the benzoic acid matches a model profile according to D. Brooke and R. J. Washkuhn (Zero-Order Drug Delivery System: Theory and Preliminary Testing, J Pharm Sci., 1977, 66:159-162) and was controlled by the interface. Therefore, a controlled release profile can be designed according to the dosage forms disclosed herein.

Example 2

This example illustrates a design of dosage form that controls release of drug contents from different compartments.

Figure 19A:
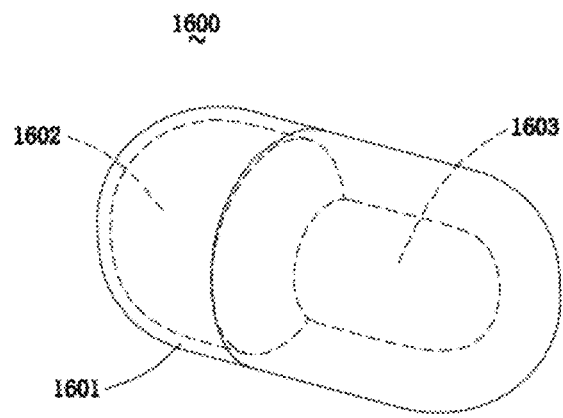
FIG. 19A shows the perspective view of a dosage form that contains two compartments.
Figure 19B:
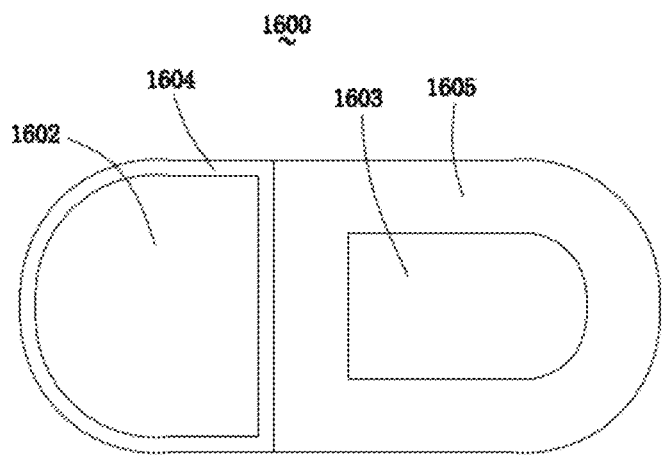
FIG. 19B shows the cross-sectional view of the dosage form of FIG. 19A.

Dosage design: two dosage forms were produced using fused deposition modeling methods. The substrate of the dosage forms was made of Copovidone (Kollidon® VA64) 72%, PEG1500 18% and Soluplus® 10%. The drug content was consisted of Moxifloxacin Hydrochloride 30%, PEG1000 70%. The schematic of the dosage forms are illustrated in FIGS. 19A and 19B. Referring to FIGS. 19A and 19B, the dosage form 1600 contained a substrate 1601 that forms two compartments 1602 and 1603. The compartments were enclosed by a wall 1604 and 1605, respectively. For the first dosage form, the two compartments were enclosed by walls having a thickness of 0.75 mm and 1.5 mm, respectively. For the second dosage form, the two compartments were enclosed by walls having a thickness of 0.75 mm and 2.25 mm, respectively.

To detect the release of the drug content, the dosage form was added to 900 ml phosphate buffer of pH6.8 at 100 rpm. The UV absorption of the buffer was assayed to determine the release of the drug content.

Figure 19C:
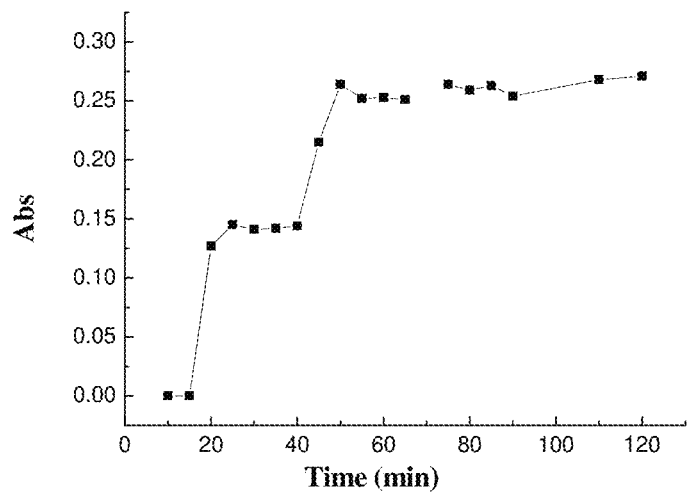
FIG. 19C shows an exemplary release profile of the dosage form of FIG. 19A.
Figure 19D:
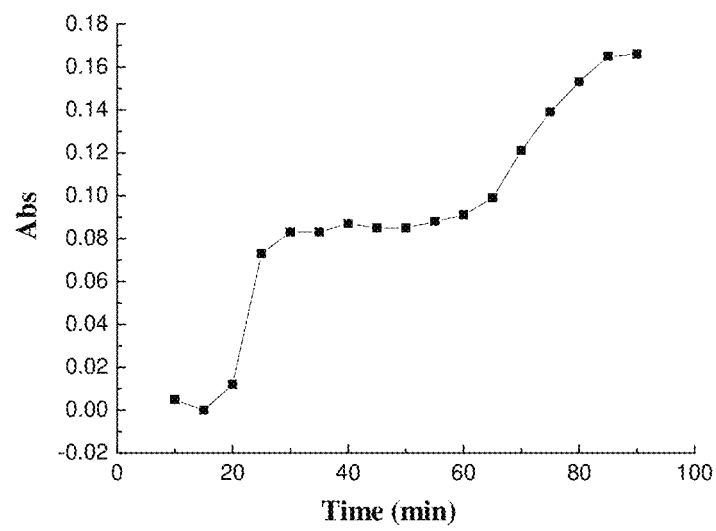
FIG. 19D shows another exemplary release profile of the dosage form of FIG. 19A.

The results of the release assays were illustrated in FIGS. 19C and 19D. As shown in FIG. 19C, when the first dosage form was added to the buffer for 20 min, the first compartment was open, and the drug content in the first compartment was released. The second compartment was not open till 40 min after the dosage form was added to the buffer. For the second dosage form, whose results were illustrated in FIG. 19D, the second compartment was not open till 60 min after the dosage form was added to the buffer. Therefore, the release profile of the dosage form can be controlled through the thickness of the wall that encloses a compartment.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

TABLE 1

| Polymer | Vendor | Commercial Name | Chemical Structure | Water Solubility |
|---|---|---|---|---|
| Polyvinyl caprolactam-polyvinyl acetate-polyethylene glycol graft copolymer 57/30/13 | BASF SE, Germany | Soluplus | 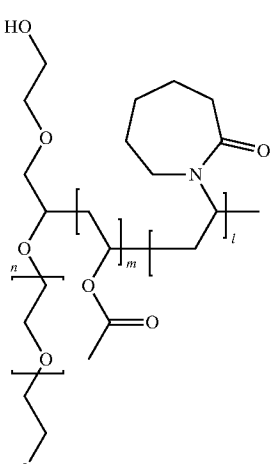<br>Amphiphilic | 25 w/w % |

TABLE 1-continued

| Polymer | Vendor | Commercial Name | Chemical Structure | Water Solubility |
|---|---|---|---|---|
| | | Soluplus + 10% Plasticizer Kolliphor P 188 | (structure shown) | 40 w/w % (freely soluble) |
| | | Soluplus + 10% Plasticizer Kolliphor RH40 | n/a | poorly soluble |
| | | Soluplus+10% Plasticizer PEG 1500 | (structure shown) | soluble |
| Polyvinylpyrrolidone-co-vinyl-acetate (PVP-VA) | International Specialty Products Inc., Manchester, UK | PVP/VA | | 40 w/w % (freely soluble) |
| | International Specialty Products Inc., Wayne, NJ, USA | Plasdone S-630 | (structure shown) | 40 w/w % (freely soluble) |
| Polyvinylpyrrolidone-polyvinyl acetate copolymer (PVP-VA) 60/40 | BASF SE, Germany | Kollidon VA 64 | | 40 w/w % (freely soluble) |
| Polyvinylpyrrolidone-polyvinyl acetate copolymer (PVP-VA) 60/40 | BASF SE, Germany | Kollidon VA 64 + 10% Plasticizer Kolliphor P 188 | (structure shown) | 40 w/w% (freely soluble) |
| Polyvinylpyrrolidone-polyvinyl acetate copolymer (PVP-VA) 60/40 | BASF SE, Germany | Kollidon VA 64 + 10% Plasticizer Kolliphor RH40 | n/a | poorly soluble |
| Polyvinylpyrrolidone-polyvinyl acetate copolymer (PVP-VA) 60/40 | BASF SE, Germany | Kollidon VA 64 + 10% Plasticizer PEG 1500 | (structure shown) | soluble |
| Polyvinylpyrrolidone (PVP) | International Specialty Products Inc., Wayne, NJ, USA | Plasdone K-29/32 PVP K30 | | soluble |
| PVP | | polyvinyl-pyrrolidone k30 | | soluble |
| PVP | | Polyvinyl-pyrrolidone K25 (PVP K25) | | soluble |
| PVP | | PVP K25+ Plasticizer dibutyl sebacate (DBS) | (structure shown) | soluble |
| PVP | | PVP K25 + Plasticizer Triethyl citrate (TEC) | | |
| PVP | | Kollidon 12 PF | | |

TABLE 1-continued

| Polymer | Vendor | Commercial Name | Chemical Structure | Water Solubility |
|---|---|---|---|---|
| PVP | | Kollidon 12 PF + 10% Plasticizer Kolliphor P 188 | $H{-}[O{-}CH_2CH_2]_x{-}[O{-}CH(CH_3)CH_2]_y{-}[O{-}CH_2CH_2]_z{-}OH$ | 40 w/w % (freely soluble) |
| PVP | | Kollidon 12 PF + 10% Plasticizer Kolliphor RH40 | n/a | 40 w/w % (freely soluble) |
| PVP | | Kollidon 12 PF + 10% Plasticizer PEG 1500 | $H{-}[O{-}CH_2CH_2]_n{-}OH$ | poorly soluble |
| PVP | | Kollidon 17 PF | | soluble |
| PVP | | Kollidon 17 PF + 10% Plasticizer Kolliphor P 188 | $H{-}[O{-}CH_2CH_2]_x{-}[O{-}CH(CH_3)CH_2]_y{-}[O{-}CH_2CH_2]_z{-}OH$ | 40 w/w % (freely soluble) |
| PVP | | Kollidon 17 PF + 10% Plasticizer Kolliphor RH40 | n/a | 40 w/w % (freely soluble) |
| PVP | | Kollidon 17 PF + 10% Plasticizer PEG 1500 | $H{-}[O{-}CH_2CH_2]_n{-}OH$ | poorly soluble |
| Spray formulated mixture of polyvinyl acetate (PVAc) and polyvinylpyrrolidone (PVP) 80/20 | BASF SE, Germany | Kollidon SR | [polyvinyl acetate]$_n$ and [polyvinylpyrrolidone]$_m$ | 0 (Because PVAc is lipophilic and water insoluble?) |
| Spray formulated mixture of polyvinyl acetate (PVAc) and polyvinylpyrrolidone (PVP) 80/20 | BASF SE, Germany | Kollidon SR + 10% Plasticizer Kolliphor P 188 | $H{-}[O{-}CH_2CH_2]_x{-}[O{-}CH(CH_3)CH_2]_y{-}[O{-}CH_2CH_2]_z{-}OH$ | 40 w/w % (freely soluble) |
| Spray formulated mixture of polyvinyl acetate (PVAc) and polyvinylpyrrolidone (PVP) 80/20 | BASF SE, Germany | Kollidon SR + 10% Plasticizer Kolliphor RH40 | n/a | poorly soluble |
| Spray formulated mixture of polyvinyl acetate (PVAc) and polyvinylpyrrolidone (PVP) 80/20 | BASF SE, Germany | Kollidon SR + 10% Plasticizer PEG 1500 | $H{-}[O{-}CH_2CH_2]_n{-}OH$ | soluble |
| Polyethylene glycol-polyvinyl alcohol graft copolymer 25/75 | BASF SE, Germany | Kollicoat IR | PEG-PVA graft copolymer structure with segments $m$, $n$, $p$ | 40 w/w % (freely soluble) |
| Polyethylene glycol-polyvinyl alcohol graft copolymer 25/75 | BASF SE, Germany | Kollicoat IR + 10% Plasticizer PEG 1500 | $H{-}[O{-}CH_2CH_2]_x{-}[O{-}CH(CH_3)CH_2]_y{-}[O{-}CH_2CH_2]_z{-}OH$ | soluble |

TABLE 1-continued

| Polymer | Vendor | Commercial Name | Chemical Structure | Water Solubility |
|---|---|---|---|---|
| Kollicoat IR-polyvinyl alcohol 60/40 | BASF SE, Germany | Kollicoat Protect | 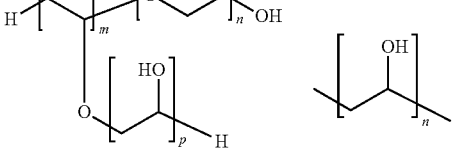 | 25 w/w % |
| Kollicoat IR-polyvinyl alcohol 60/40 | BASF SE, Germany | Kollicoat Protect + 10% Plasticizer PEG 1500 | 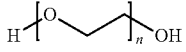 | soluble |
| Polyvinyl Alcohol (PVA or PV-OH) | DuPont Company, Wilmingon, Delaware USA | Elvanol ® | 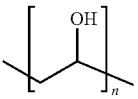 | soluble |
| Hydroxypropyl cellulose (HPC) | Ashland Aqualon Functional Ingredients, Wilmington, DE, USA | Klucel EF | 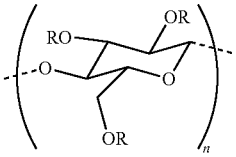 R = H or $CH_2CH(OH)CH_3$ | soluble |
|  |  | Klucel ELF | R = H or $CH_2CH(OH)CH_3$ |  |
| Ethyl cellulose (EC) | Dow Chemical, Midland, MI, US | Ethocel ® | 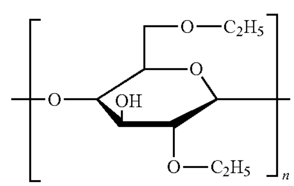 | soluble |
| Poly(ethylene oxide) (PEO) | Sigma-Aldrich Ltd, Poole, Dorset, UK | Polyox ® WSR | 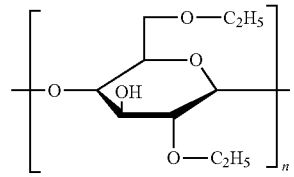 | Soluble |
| Poly(ethylene glycol) (PEG) | Dow Chemical, Midland, MI, US | Carbowax ® | 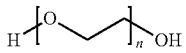 | Soluble |
| Hyperbranched Polyesteramide | Polymer Factory, Stockholm, Sweden | Hybrane S1200 | 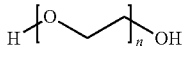 | Soluble |

TABLE 1-continued

| Polymer | Vendor | Commercial Name | Chemical Structure | Water Solubility |
|---|---|---|---|---|
| Hydroxypropyl Methylcellulose or Hypromellose (HMPC) | Dow Chemical, Midland, MI, US | Methocel ® E4M, K4M, K15M | Hydroxypropyl Methylcellulose METHOCEL E, METHOCEL F, METHOCEL J and METHOCEL K brand products | Soluble |
| Hydroxypropyl Methylcellulose or Hypromellose (HMPC) | Colorcon Inc,. Shanghai, China | HPMC (2910 grade) | $R = H, CH_3$ or $-[CH(CH_3)CH_2O]_x H$   HPMC | Soluble |
| Hydroxypropyl Methylcellulose or Hypromellose (HMPC) | Syntapharm GmbH, Mülheim-Ruhr, Germany | Pharmacoat ® 603 and 615 | $R = H, CH_3$ or $-[CH(CH_3)CH_2O]_x H$   HPMC | Soluble |
| Hydroxypropyl Methylcellulose or Hypromellose (HMPC) | Shin-Etsu Co., Ltd,. Niigata, Japan | Pharmacoat ® 603 (2910 grade) | $R = H, CH_3$ or $-[CH(CH_3)CH_2O]_x H$   HPMC | Soluble |
| Carbomer | Lubrizol Advanced Materials Inc., Cleveland, OH, US | Carbopol ® 974P + Eudragit L-100-55 | $-[CH_2-CH(COOH)]_n-$ | Soluble |

TABLE 1-continued

| Polymer | Vendor | Commercial Name | Chemical Structure | Water Solubility |
|---|---|---|---|---|
| Lactose | Quest International, Hoffman Estates, IL, USA | Lactose Anhydrate DT NF | 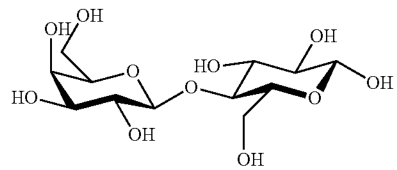 | soluble |
| Microcrystalline cellulose (MCC) | FMC, Philadelphia, PA, USA | Avicel ® PH 101 | 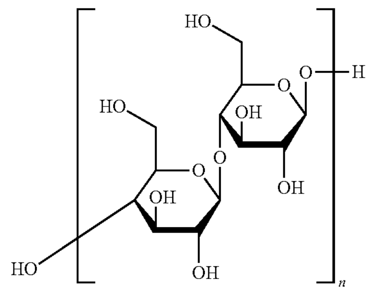 | soluble |
| Dibasic calcium phosphate | Penwest Pharmaceuticals, Patterson, NY | Emcompress ® | 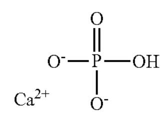 | soluble |
| Xanthan gum | CP Kelco U.S. Inc., Chicago, IL, USA | XANTURAL ® 180 | 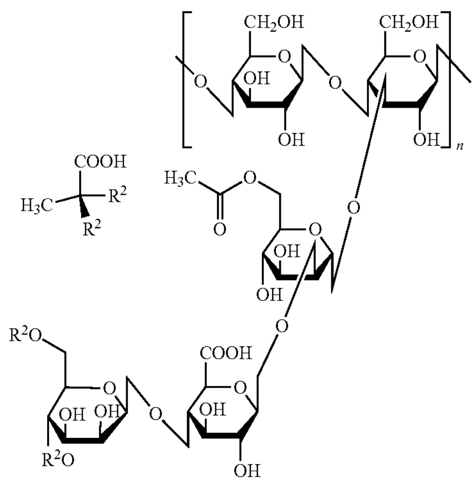 | soluble |
| Poly(methyl acrylate-co-methyl methactylate-co-methacrylic acid) 7:3:1 | Evonik Röhm GmbH, Darmstadt, Germany | Eudragit ® 4135F + Plasticizer PEG8000 | | |
| Poly(methyl acrylate-co-methyl methactylate-co-methacrylic acid) 7:3:1 | Evonik Röhm GmbH, Darmstadt, Germany | Eudragit ® 4155F (freeze dried EUDRAGIT ® FS 30 D) | | soluble at pH > 7 |
| Poly(methacrylic acid-co-methylmethacrylate) | Evonik Industries, Piscataway, | Eudragit ® S | | |

TABLE 1-continued

| Polymer | Vendor | Commercial Name | Chemical Structure | Water Solubility |
|---|---|---|---|---|
| 1:2 | New Jersey, USA | | | |
| Poly(methacrylic acid-co-methylmethacrylate) 1:2 | Evonik Industries, Piscataway, New Jersey, USA | Eudragit ® S + Plasticizer Triethyl citrate (TEC) | | |
| Poly(methacrylic acid-co-methylmethacrylate) 1:2 | Evonik Industries, Piscataway, New Jersey, USA | Eudragit ® S + Plasticizer PEG 8000 | | |
| Poly(methacrylic acid-co-methylmethacrylate) 1:2 | Evonik Industries, Piscataway, New Jersey, USA | Eudragit ® S + Plasticizer methylparaben | | soluble at pH > 7 [36] |
| Poly(methacylic acid-co-ethyl acrylate) 1:1 | Evonik Degussa Piscataway, NJ | Eudragit L-100-55 | 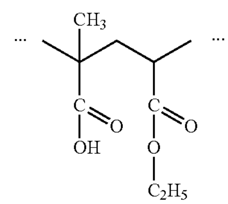 | Soluble at pH > 5.5 |
| Poly(methacylic acid-co-methyl acrylate) 1:1 | Evonik Degussa Piscataway, NJ | Eudragit L-100 | 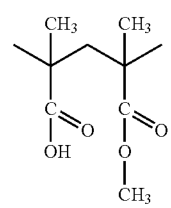 | Soluble at pH > 6.0 |
| Hydroxypropyl Methylcellulose Phthalate or Hypromellose phthalate | Shin-Etsu Co., Ltd., Niigata, Japan | HP-55F | 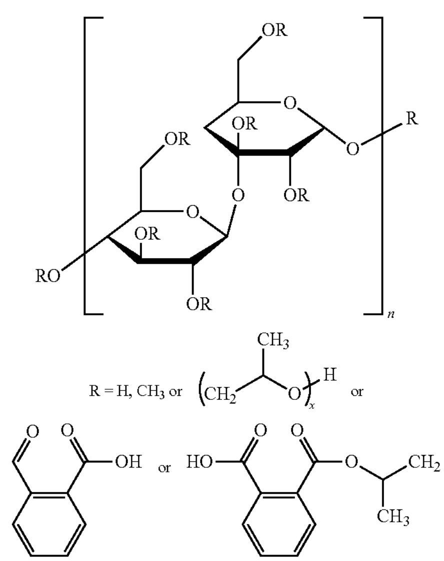 | Soluble at pH > 5.5 |

TABLE 1-continued

| Polymer | Vendor | Commercial Name | Chemical Structure | Water Solubility |
|---|---|---|---|---|
| Hydroxypropyl Methylcellulose Acetate Succinate or Hypromellose Acetate Succinate (HPMCAS) | Shin-Etsu Co., Ltd., Niigata, Japan | Shin-Etsu Aqoat MF | (cellulose backbone with OR and CH₂OR substituents) R = —H, —CH₃, —CH₂CH(CH₃)CH, —COCH₃, —COCH₂CH₂COOH, —CH₂CH(CH₃)COOCH₃, —CH₂CH(CH₃)OCOCH₂CH₂COOH | Soluble at pH > 6.0 |
| Hydroxypropyl Methylcellulose Acetate Succinate or Hypromellose Acetate Succinate (HPMCAS) | Shin-Etsu Co., Ltd., Niigata, Japan | Shin-Etsu Aqoat LF | | Soluble at pH > 5.5 |
| Poly(dimethylaminoethyl-methacrylate-co-methacrylic esters) | Rohm GmbH & Co., Darmstadt, Germany | Eudragit IE | | Soluble at pH < 5 |
| Hydroxypropyl Methylcellulose Acetate Succinate or Hypromellose Acetate Succinate (HPMCAS) | Shin-Etsu Co., Ltd., Niigata, Japan | Shin-Etsu Aqoat MF | | Soluble at pH > 6.0 |
| Poly(lactide-co-glycolide) | Birmingham Polymers, Inc., Birmingham, AL, USA | PLGA | [—CH(CH₃)—C(=O)—O—]$_x$[—CH₂—C(=O)—O—]$_y$ | insoluble |
| | | Elvax ® 40W: EV28 | ethylene-vinyl acetate copolymer structure | insoluble |
| | | Elvax ® 40W: EV9 | ethylene-vinyl acetate copolymer structure | insoluble |
| | | Evatane ® | ethylene-vinyl acetate copolymer structure | insoluble |
| Polyethylene (PE) | Scientific Polymer Products Inc., Ontario, NY | PE1400 | [—CH₂—CH₂—]$_n$ | insoluble |
| Polycaprolactone (PCL) | Scientific Polymer Products Inc., Ontario, NY | — | [—(CH₂)₅—C(=O)—O—]$_n$ | insoluble |

TABLE 1-continued

| Polymer | Vendor | Commercial Name | Chemical Structure | Water Solubility |
|---|---|---|---|---|
| Carnauba Wax | Noda Wax Co., Japan | — | n/a | insoluble |
| Glyceryl Palmitostearate | Gattefosse, Cedex, France | Precirol ® ATO 5 | | insoluble |
| Hydrogenated Castor & Soybean Oil | Abitec Corporation, Janesville WI, USA | Sterotex ® K | n/a | insoluble |
| Cellulose acetate butyrate (CAB) | Eastman Chemical Company, Kingsport, Tennessee, USA | CAB 381-0.5 | 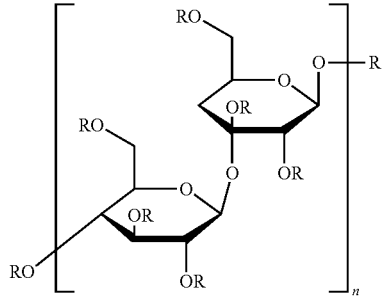 | insoluble |
| CAB | FMC, Newark, DE, USA | CAB 500-1 | 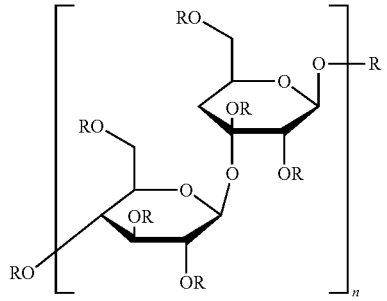 | insoluble |
| Poly(vinyl acetate) (PVAc) | Scientific Polymer Products Inc., Ontario, NY | Sentry ® plus | 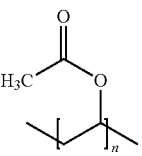 | insoluble |

TABLE 1-continued

| Polymer | Vendor | Commercial Name | Chemical Structure | Water Solubility |
|---|---|---|---|---|
| Poly(ethyl acrylate-co-methyl methacrylate-co-trimethylammonioethyl methacrylate chloride) | Rohm GmbH & Co., Darmstadt, Germany | Eudragit RS PO (1:2:0.1) | 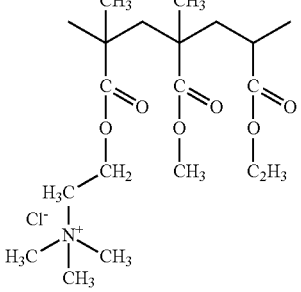 | insoluble |
| Poly(ethyl acrylate-co-methyl methacrylate-co-trimethylammonioethyl methacrylate chloride) | Rohm GmbH & Co., Darmstadt, Germany | Eudragit RL PO (1:2:0.2) | 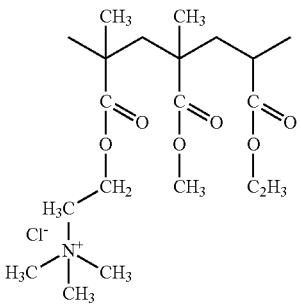 | insoluble |

What is claimed is:

1. A tablet comprising:
   i) a first substrate layer, a second substrate layer, and a third substrate layer, wherein each substrate layer comprises a substrate;
   ii) a first nanoparticle layer comprising nanoparticles consisting of a first drug; and
   iii) a second nanoparticle layer comprising nanoparticles consisting of a second drug;
   wherein the tablet has a multi-layered structure from top to bottom: the first substrate layer, the first nanoparticle layer, the second substrate layer, the second nanoparticle layer, and the third substrate layer; and
   wherein the first drug and the second drug are capable of being continuously released from a lateral side of the tablet.

2. The tablet of claim 1, wherein the first drug and the second drug are different.

3. The tablet of claim 1, wherein the first drug and the second drug are the same.

4. The tablet of claim 1, wherein the substrate of each substrate layer is erodible.

5. The tablet of claim 1, wherein the substrate thickness is different among each substrate layer.

6. The tablet of claim 1, wherein the substrate thickness is the same among each substrate layer.

7. The tablet of claim 1, wherein the substrate of each substrate layer comprises a drug embedded therein.

8. The tablet of claim 7, wherein the drug embedded within the substrate of each substrate layer is different.

9. The tablet of claim 7, wherein the drug embedded within the substrate of each substrate layer is the same.

10. The tablet of claim 1, wherein the size of the nanoparticles of the first drug and the second drug is from about 1 nm to about 900 nm.

11. The tablet of claim 10, wherein the size of the nanoparticles of the first drug and the second drug is from about 100 nm to about 500 nm.

12. The tablet of claim 11, wherein the size of the nanoparticles of the first drug and the second drug is from about 100 nm to about 200 nm.

13. The tablet of claim 1, wherein the tablet is produced by three-dimensional (3D) printing.

14. The tablet of claim 1, wherein the nanoparticles of the first drug and the second drug have the same size.

15. The tablet of claim 1, wherein the nanoparticles of the first drug and the second drug have different sizes.

16. The tablet of claim 1, wherein the substrate of each substrate layer is a thermoplastic material.

17. The tablet of claim 16, wherein the substrate of each substrate layer is independently selected from the group consisting of polyvinyl caprolactam-polyvinyl acetate-polyethylene glycol graft copolymer 57/30/13, polyvinylpyrrolidone-co-vinyl-acetate, polyvinylpyrrolidone-polyvinyl acetate copolymer (PVP-VA) 60/40, polyvinylpyrrolidone (PVP), polyvinyl alcohol (PVA or PV-OH), poly(ethylene glycol) (PEG), hydroxypropyl methylcellulose or hypromellose (HMPC), hydroxypropyl methylcellulose acetate succinate or hypromellose acetate succinate (HPMCAS), carbomer, hydroxyl propyl cellulose (HPC), Poloxamer, Sucrose, Glucose, and a combination thereof.

18. The tablet of claim 1, wherein the first nanoparticle layer and the second nanoparticle layer are exposed on the lateral side of the tablet.

19. The tablet of claim 1, wherein the tablet further comprises a coating.

* * * * *